United States Patent

Wang et al.

(10) Patent No.: US 9,276,911 B2
(45) Date of Patent: Mar. 1, 2016

(54) SECURE AND SCALABLE MAPPING OF HUMAN SEQUENCING READS ON HYBRID CLOUDS

(75) Inventors: XiaoFeng Wang, Bloomington, IN (US); Haixu Tang, Bloomington, IN (US); Yangyi Chen, Bloomington, IN (US); Bo Peng, Bloomington, IN (US)

(73) Assignee: Indiana University Research & Technology Corporation, Indianapolis, IN (US)

( * ) Notice: Subject to any disclaimer, the term of this patent is extended or adjusted under 35 U.S.C. 154(b) by 45 days.

(21) Appl. No.: 14/116,343

(22) PCT Filed: May 14, 2012

(86) PCT No.: PCT/US2012/037791
§ 371 (c)(1),
(2), (4) Date: Nov. 7, 2013

(87) PCT Pub. No.: WO2012/158621
PCT Pub. Date: Nov. 22, 2012

(65) Prior Publication Data
US 2014/0075183 A1 Mar. 13, 2014

Related U.S. Application Data

(60) Provisional application No. 61/485,867, filed on May 13, 2011.

(51) Int. Cl.
*H04L 29/06* (2006.01)
*G06F 19/22* (2011.01)
(Continued)

(52) U.S. Cl.
CPC ............ *H04L 63/0428* (2013.01); *G06F 19/22* (2013.01); *G06F 19/28* (2013.01); *H04L 9/0637* (2013.01); *H04L 9/3239* (2013.01)

(58) Field of Classification Search
CPC ......... G06F 19/22; G06F 19/28; G06F 21/32; G06F 21/64; H04L 63/0428; H04L 9/0637; H04L 9/3239; H04L 9/3223; G07C 9/00087
See application file for complete search history.

(56) References Cited

U.S. PATENT DOCUMENTS

| 6,531,316 B1 | 3/2003 | Patten et al. |
| 7,209,561 B1 | 4/2007 | Shankar et al. |

(Continued)

FOREIGN PATENT DOCUMENTS

WO    2010/129301 A2    11/2010

OTHER PUBLICATIONS

International Searching Authority, International Search Report and Written Opinion for PCT/US2012/037791, Jul. 10, 2012, 9 pages.

(Continued)

*Primary Examiner* — Ali Abyaneh
*Assistant Examiner* — Vance Little
(74) *Attorney, Agent, or Firm* — Barnes & Thornburg LLP

(57) ABSTRACT

System and methods are provided for performing privacy-preserving, high-performance, and scalable DNA read mapping on hybrid clouds including a public cloud and a private cloud. The systems and methods offer strong privacy protection and have the capacity to process millions of reads and allocate most of the workload to the public cloud at a small overall cost. The systems and methods perform seeding on the public cloud using keyed hash values of individual sequencing reads' seeds and then extend matched seeds on the private cloud. The systems and methods are designed to move the workload of read mapping from the extension stage to the seeding stage, thereby ensuring that the dominant portion of the overhead is shouldered by the public cloud.

5 Claims, 9 Drawing Sheets

(51) Int. Cl.
*G06F 19/28* (2011.01)
*H04L 9/06* (2006.01)
*H04L 9/32* (2006.01)

(56) References Cited

U.S. PATENT DOCUMENTS

| | | | |
|---|---|---|---|
| 7,636,703 B2* | 12/2009 | Taylor | 706/62 |
| 2001/0039497 A1* | 11/2001 | Hubbard | 705/1 |
| 2002/0197635 A1* | 12/2002 | Kato et al. | 435/6 |
| 2003/0120429 A1* | 6/2003 | Li et al. | 702/19 |
| 2003/0200033 A1* | 10/2003 | Segal et al. | 702/20 |
| 2004/0006433 A1* | 1/2004 | Robson et al. | 702/20 |

OTHER PUBLICATIONS

Y. Chen et al., "Large-Scale Privacy-Preserving Mapping of Human Genomic Sequences on Hybrid Clouds," Proceedings of the 19th Network & Distributed System Security Symposium, Feb. 6, 2012, 18 pages.

\* cited by examiner

SECURE AND SCALABLE MAPPING OF HUMAN SEQUENCING READS ON HYBRID CLOUDS

CROSS-REFERENCE TO RELATED APPLICATIONS

This application is a U.S. national counterpart application of International Application Serial No. PCT/US2012/037791, filed May 14, 2012, which claims the benefit of U.S. Provisional Patent Application Ser. No. 61/485,867, filed May 13, 2011. The entire disclosures of both of the foregoing applications are hereby incorporated by reference.

STATEMENT REGARDING FEDERALLY SPONSORED RESEARCH

This invention was made with government support under CNS-0716292, CNS-1017782, and CNS-1223495 awarded by the National Science Foundation. The Government has certain rights in the invention.

BACKGROUND

1. Field of the Disclosure

The present disclosure relates to DNA read mapping. More specifically the present disclosure relates to DNA read mapping utilizing cloud computing, for example a commercial cloud computing service.

2. Description of the Related Art

The rapid advance of human genomics technologies has not only revolutionized life science but also profoundly impacted the development of computing technologies. At the core of this scientific revolution is the emergence of the high-throughput sequencing technologies (often collectively referred to as Next Generation Sequencing (NGS)). Today, a single sequencer can generate millions of short DNA sequences (called reads), each read comprising a 30 to 120 base-pair long sequence of a genome having over a billion nucleotides. To interpret read sequences, the reads are aligned with publicly available human DNA sequences (called reference genomes). The positions of the reads (within a reference genome) and other features (e.g., whether the sequence is of a human or microbes associated with a human) are thereby able to be identified in this step, known as read mapping.

Read mapping is, in general, a prerequisite for most DNA sequence analysis, and is an important analysis for sequencing human DNA. The analysis, in general, involves intensive computation given the huge size of the reference genome (6 billion nucleotides) and the complexity of the mapping operation. Read mapping includes calculating edit distances between reads and all the substrings on the reference genome. As such, read mapping is time and labor intensive and often expensive.

With the fast-growing sequence data produced by NGS, the demands for mapping such data are increasingly hard to be met by the computing power within organizations. To meet this demand, outsourcing read mapping to low-cost commercial clouds, for example Amazon Elastic Compute Cloud (EC2) which can process terabytes of data at a low price (e.g., 0.1 dollar per CPU hour), is one option previously considered for handling this large, data sensitive task. However, commercial cloud outsourcing creates a serious privacy risk regarding sequence information and identity information of the sequence donors which may lead to denied access to health/life/disability insurance and educational/employment opportunities. Previously explored commercial computing techniques for read mapping have lacked the capability of scalability of read mapping while protecting the identification information from attacks. In recognition of the short-fall of current options, in order to protect sequence donors, the National Institutes of Health (NIH) has thus far disallowed any datasets involving human DNA to be handed over to the public cloud.

Another previously explored avenue for addressing this problem includes secure computation outsourcing (SCO). However, existing approaches have thus far not been able to enable secure read mapping on a commercial cloud. Traditional techniques of SCO, such as homomorphic encryption, secret sharing, and secure multi-party computation (SMC), are too heavyweight to sustain a data intensive computation involving terabytes of data, that is to say that the computational time needed for processing each piece of data makes the SCO impractical for most application. For example, a privacy-preserving protocol previously proposed takes 3 minutes to calculate the edit distance between two 25-element sequences through homomorphic encryption and oblivious transfers. Other secret-sharing based approaches all require an immense amount of data exchanged between different share holders during a computation, and are therefore hard to scale. In addition, secret sharing techniques do not relieve the NIH of the above-mentioned legal burdens, which cloud providers are either unwilling to undertake or must significantly raise prices of services in response.

SUMMARY

The system and method of the instant disclosure provides privacy-preserving, high-performance, and scalable DNA read mapping on hybrid clouds which include a public cloud and a private cloud. This approach offers strong privacy protection, and has the capacity to process millions of reads and allocate most of the workload to the public cloud at a small overall cost. Further, this system performs seeding on the public cloud using keyed hash values of individual sequencing reads' seeds, and then extends matched seeds on the private cloud. The system and method are designed to move the workload of read mapping from the extension stage to the seeding, thereby ensuring that the dominant portion of the overheads is shouldered by the public cloud. Thus, the technique achieves privacy-preserving and scalable read mapping on hybrid clouds that allows for outsourcing read mapping to low-cost commercial clouds in a manner that is useful and protects the identity of donors.

The system and method of the instant disclosure are based upon the well-known seed-and-extend strategy, which first matches a seed, a segment of a read with one-(d+1)th of the read's length given an edit distance d, to the substrings on the reference genome, and then extends from these substrings to align the whole read. Thus, the mapping task is split along two stages, delegating them to public and private clouds respectively: the public cloud searches for the exact matches between the keyed hash values of seeds and substrings (called l-mers for a substring of length l) on the reference genome to determine the possible positions of reads, while the private cloud extends from these positions to find the optimal alignments of these reads.

While a single extension operation (involving calculation of an edit distance under a threshold) is known to be extremely efficient (in linear time), a read-mapping task is typically burdened by a huge number of extensions that need to be made. Therefore, it is conceivable that once the seeding process yields only a few or even unique positions for each read, the workload of the extension stage, which is undertaken by the private cloud, becomes much lower than that of the public cloud. This is not guaranteed by the traditional "seed and extend" approach, particularly when the seed is too short, due to a relatively large edit distance (e.g., 6 for 100-base pair (bp) reads). To address this challenge, the disclosed system utilizes seed combinations to ensure a small number of extensions for each read, at a spatial overhead that may be easily afforded by today's clouds. The inventors conducted a security analysis of the instant system and method over the reference genome and a performance analysis on a cloud platform using real human microbiome datasets. This approach mapped 10 million reads to the largest human chromosome within half an hour and outsourced over 98% of the mapping computation to the low-cost public cloud.

A prototype of the disclosed system and method was implemented over Hadoop, a popular MapReduce platform, and a thorough security and performance evaluation was performed using real human microbiome data on FutureGrid, a large-scale, across-the-country cloud test-bed.

A focus of the disclosed system and method is confidentiality, as it is the main hurdle to outsourcing read-mapping computation to the public cloud and therefore urgently needs practical solutions. Although integrity of cloud computing is no doubt important, so far people are willing to live with the risk that their tasks may not be handled correctly by the cloud. This is evidenced by the fact that mapping of non-human reads already happened on EC2, while the tasks involving human data are still not allowed to be given to the public cloud.

According to an embodiment of the present disclosure, a method for analyzing a plurality of DNA sequence reads is disclosed. The method comprises the steps of: partitioning each of a plurality of DNA sequence reads into a plurality of seeds; encrypting each of the plurality of seeds; comparing a plurality of the encrypted plurality of seeds to a reference genome; identifying a location in the reference genome which matches the plurality of the encrypted plurality of seeds, said steps of comparing and identifying performed in a public computing environment wherein the plurality of the encrypted plurality of seeds are exposed to at least one computing network outside a user computing network; and extending the seeds from the locations in the reference genome indentified in said step of indentifying, said step of extending performed in a private computing environment wherein the seed being extended is not exposed to other computing networks outside the computing network of the user.

According to another embodiment of the present disclosure, a system is presented for analyzing a plurality of DNA sequence reads. The system comprises: a user computing network having a processor and a memory including a plurality of computer readable instructions stored thereon, the computer readable instructions executable by the processor such that when executed by the processor cause the processor to: partition a plurality of DNA sequence reads into a plurality of sequence seeds; encrypt at least a plurality of the seeds; and compare at least a plurality of the seeds with a reference genome; and an external computing network external configured to communicate with the user computing network, the external computing network having a processor and a memory including the reference genome stored thereon and a plurality of computer executable instructions stored thereon, such that when executed by the processor cause the processor to identify a location in the reference genome which matches the seeds and communicate the location to the user computing network. The user computing network extends the seeds from the locations in the reference genome identified as matching the seeds.

BRIEF DESCRIPTION OF THE DRAWINGS

The above-mentioned and other features and advantages of this disclosure, and the manner of attaining them, will become more apparent and the disclosure itself will be better understood by reference to the following description of embodiments of the disclosure taken in conjunction with the accompanying drawings, wherein.

Corresponding reference characters indicate corresponding parts throughout the several views. The exemplifications set out herein illustrate exemplary embodiments of the disclosure and such exemplifications are not to be construed as limiting the scope of the disclosure in any manner.

DETAILED DESCRIPTION

Figure 1A:
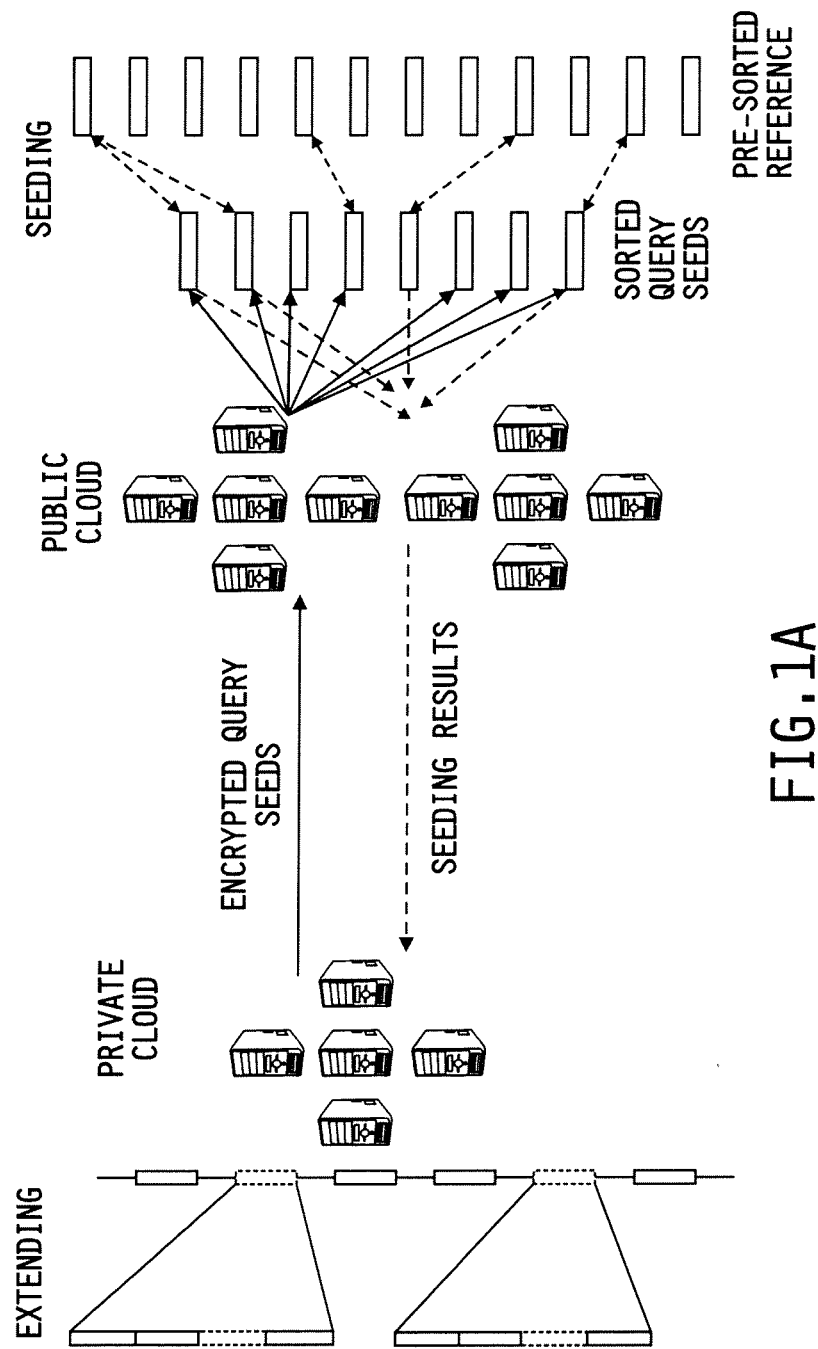
FIG. 1a is a schematic illustration of an embodiment of the present disclosure.

The detailed descriptions which follow are presented in part in terms of algorithms and symbolic representations of operations on data bits within a computer memory representing alphanumeric characters or other information. These descriptions and representations are the means used by those skilled in the art of data processing arts to most effectively convey the substance of their work to others skilled in the art.

An algorithm is here, and generally, conceived to be a self-consistent sequence of steps leading to a desired result. These steps are those requiring physical manipulations of physical quantities. Usually, though not necessarily, these quantities take the form of electrical or magnetic signals capable of being stored, transferred, combined, compared, and otherwise manipulated. It proves convenient at times, principally for reasons of common usage, to refer to these signals as bits, values, symbols, characters, display data, terms, numbers, or the like. It should be borne in mind, however, that all of these and similar terms are to be associated with the appropriate physical quantities and are merely used here as convenient labels applied to these quantities.

Some algorithms may use data structures for both inputting information and producing the desired result. Data structures greatly facilitate data management by data processing systems, and are not accessible except through sophisticated software systems. Data structures are not the information content of a memory, rather they represent specific electronic structural elements which impart a physical organization on the information stored in memory. More than mere abstraction, the data structures are specific electrical or magnetic structural elements in memory which simultaneously represent complex data accurately and provide increased efficiency in computer operation.

Further, the manipulations performed are often referred to in terms, such as comparing or adding, commonly associated with mental operations performed by a human operator. No such capability of a human operator is necessary, or desirable in most cases, in any of the operations described herein which form part of the present disclosure; the operations are machine operations. Useful machines for performing the operations of the present disclosure include general purpose digital computers or other similar devices. In all cases the distinction between the method operations in operating a computer and the method of computation itself should be recognized. The present disclosure relates to a method and apparatus for operating a computer in processing electrical or other (e.g., mechanical, chemical) physical signals to generate other desired physical signals.

The present disclosure also relates to an apparatus for performing these operations. This apparatus may be specifically constructed for the required purposes or it may comprise a general purpose computer as selectively activated or reconfigured by a computer program stored in the computer. The algorithms presented herein are not inherently related to any particular computer or other apparatus. In particular, various general purpose machines may be used with programs written in accordance with the teachings herein, or it may prove more convenient to construct more specialized apparatus to perform the required method steps. The required structure for a variety of these machines will appear from the description below.

The present disclosure deals with "object-oriented" software, and particularly with an "object-oriented" operating system. The "object-oriented" software is organized into "objects", each comprising a block of computer instructions describing various procedures ("methods") to be performed in response to "messages" sent to the object or "events" which occur with the object. Such operations include, for example, the manipulation of variables, the activation of an object by an external event, and the transmission of one or more messages to other objects.

Messages are sent and received between objects having certain functions and knowledge to carry out processes. Messages are generated in response to user instructions, for example, by a user activating an icon with a "mouse" pointer generating an event. Also, messages may be generated by an object in response to the receipt of a message. When one of the objects receives a message, the object carries out an operation (a message procedure) corresponding to the message and, if necessary, returns a result of the operation. Each object has a region where internal states (instance variables) of the object itself are stored and where the other objects are not allowed to access. One feature of the object-oriented system is inheritance. For example, an object for drawing a "circle" on a display may inherit functions and knowledge from another object for drawing a "shape" on a display.

A programmer "programs" in an object-oriented programming language by writing individual blocks of code each of which creates an object by defining its methods. A collection of such objects adapted to communicate with one another by means of messages comprises an object-oriented program. Object-oriented computer programming facilitates the modeling of interactive systems in that each component of the system may be modeled with an object, the behavior of each component being simulated by the methods of its corresponding object, and the interactions between components being simulated by messages transmitted between objects.

An operator may stimulate a collection of interrelated objects comprising an object-oriented program by sending a message to one of the objects. The receipt of the message may cause the object to respond by carrying out predetermined functions which may include sending additional messages to one or more other objects. The other objects may in turn carry out additional functions in response to the messages they receive, including sending still more messages. In this manner, sequences of message and response may continue indefinitely or may come to an end when all messages have been responded to and no new messages are being sent. When modeling systems utilizing an object-oriented language, a programmer need only think in terms of how each component of a modeled system responds to a stimulus and not in terms of the sequence of operations to be performed in response to some stimulus. Such sequence of operations naturally flows out of the interactions between the objects in response to the stimulus and need not be preordained by the programmer.

In the following description, several terms which are used frequently have specialized meanings in the present context. The term "object" relates to a set of computer instructions and associated data which may be activated directly or indirectly by the user. The terms "windowing environment", "running in windows", and "object oriented operating system" are used to denote a computer user interface in which information is manipulated and displayed on a video display such as within bounded regions on a raster scanned video display. The terms "network", "local area network", "LAN", "wide area network", or "WAN" mean two or more computers which are connected in such a manner that messages may be transmitted between the computers. In such computer networks, typically one or more computers operate as a "server", a computer with large storage devices such as hard disk drives and communication hardware to operate peripheral devices such as printers or modems. Other computers, termed "workstations", provide a user interface so that users of computer networks may access the network resources, such as shared data files, common peripheral devices, and inter-workstation communication. Users activate computer programs or network resources to create "processes" which include both the general operation of the computer program along with specific operating characteristics determined by input variables and its environment.

The terms "desktop", "personal desktop facility", and "PDF" mean a specific user interface which presents a menu or display of objects with associated settings for the user associated with the desktop, personal desktop facility, or PDF. When the PDF accesses a network resource, which typically requires an application program to execute on the remote server, the PDF calls an Application Program Interface, or "API", to allow the user to provide commands to the network resource and observe any output. The term "Browser" refers to a program which is not necessarily apparent to the user, but which is responsible for transmitting messages between the PDF and the network server and for displaying and interacting with the network user. Browsers are designed to utilize a communications protocol for transmission of text and graphic information over a worldwide network of computers, namely the "World Wide Web" or simply the "Web". Examples of Browsers compatible with the present disclosure include the Internet Explorer program sold by Microsoft Corporation (Internet Explorer is a trademark of Microsoft Corporation), the Opera Browser program created by Opera Software ASA, or the Firefox browser program distributed by the Mozilla Foundation (Firefox is a registered trademark of the Mozilla Foundation). Although the following description details such operations in terms of a graphic user interface of a Browser, the present disclosure may be practiced with text based interfaces, or even with voice or visually activated interfaces, that have many of the functions of a graphic based Browser.

Browsers display information which is formatted in a Standard Generalized Markup Language ("SGML") or a Hyper-Text Markup Language ("HTML"), both being scripting languages which embed non-visual codes in a text document through the use of special ASCII text codes. Files in these formats may be easily transmitted across computer networks, including global information networks like the Internet, and allow the Browsers to display text, images, and play audio and video recordings. The Web utilizes these data file formats to conjunction with its communication protocol to transmit such information between servers and workstations. Browsers may also be programmed to display information provided in an eXtensible Markup Language ("XML") file, with XML files being capable of use with several Document Type Definitions ("DTD") and thus more general in nature than SGML or HTML. The XML file may be analogized to an object, as the data and the style sheet formatting are separately contained (formatting may be thought of as methods of displaying information, thus an XML file has data and an associated method).

In wireless wide area networks, communication primarily occurs through the transmission of radio signals over analog, digital cellular, or personal communications service ("PCS") networks. Signals may also be transmitted through microwaves and other electromagnetic waves. At the present time, most wireless data communication takes place across cellular systems using second generation technology such as code-division multiple access ("CDMA"), time division multiple access ("TDMA"), the Global System for Mobile Communications ("GSM"), personal digital cellular ("PDC"), or through packet-data technology over analog systems such as cellular digital packet data (CDPD") used on the Advance Mobile Phone Service ("AMPS").

The terms "wireless application protocol" or "WAP" mean a universal specification to facilitate the delivery and presentation of web-based data on handheld and mobile devices with small user interfaces. "Mobile Software" refers to the software operating system which allows for application programs to be implemented on a mobile device such as a mobile telephone or PDA. Examples of Mobile Software are Java and Java ME (Java and JavaME are trademarks of Sun Microsystems, Inc. of Santa Clara, Calif.), BREW (BREW is a registered trademark of Qualcomm Incorporated of San Diego, Calif.), Windows Mobile (Windows is a registered trademark of Microsoft Corporation of Redmond, Wash.), Palm OS (Palm is a registered trademark of Palm, Inc. of Sunnyvale, Calif.), Symbian OS (Symbian is a registered trademark of Symbian Software Limited Corporation of London, United Kingdom), ANDROID OS (ANDROID is a registered trademark of Google, Inc. of Mountain View, Calif.), and iPhone OS (iPhone is a registered trademark of Apple, Inc. of Cupertino, Calif.). "Mobile Apps" refers to software programs written for execution with Mobile Software.

A "physical" device is a material resource such as a server, network switch, or disk drive. Even though physical devices are discrete resources, they are not inherently unique. For example, random access memory (RAM) devices and a central processing unit (CPU) in a physical server may be interchangeable between like physical devices. Also, network switches may be easily exchanged with minimal impact. A "logical" device is a representation of or reference to a physical device to make the identification of a physical device unique and distinct from other physical devices. For example, network interfaces typically use a unique media access control (MAC) address. A MAC address is the logical unique identifier of a physical network interface card (NIC). A "traditional" device is a combined logical and physical device in which the logical device provides the identity of a physical device. For example, a physical NIC has its MAC address permanently affixed so the physical device is inextricably tied to the logical device.

A "virtualized" device breaks the traditional interdependence between physical and logical devices. Virtualization allows logical devices to exist as an abstraction without being directly tied to a specific physical device. Simple virtualization may be achieved using only logical identifiers rather than having any reliance on physical identifiers. For example, using an Internet Uniform Resource Locator (URL) instead of a server's MAC address for network identification effectively virtualizes the target server. Complex virtualization separates physical device dependencies from the logical device. For example, a virtualized NIC may have an assigned MAC address that exists independently of the physical resources managing the NIC network traffic.

A "server cloud" or "cloud" is a collection of logical devices which may or may not include underlying physical servers. The essential element of a cloud is that all logical devices in the cloud may be accessed without any knowledge or with limited knowledge of the underlying physical devices within the cloud. Fundamentally, a cloud has persistent logical resources, but is non-deterministic in its use of physical resources. For example, the Internet may be viewed as a cloud because two computers using logical names may reliably communicate even though the physical network is constantly changing.

A "virtualized logical server cloud" refers to a logical server cloud comprising multiple logical servers, where each logical server is linked to one of a bank of physical servers. The boundary of the logical server cloud is defined by the physical resources controlled by a "cloud management infrastructure" or a "server cloud manager" or SCM. The server cloud manager typically has the authority to allocate physical resources to maintain the logical server cloud; consequently, the logical server cloud does not exceed the scope of physical resources under management control. Specifically, the physical servers controlled by the SCM determine a logical server cloud's boundary. Resource manager software (RM) may act under the direction of the SCM. A RM's authority may be limited in scope—typically being task-specific. For example, a RM may be defined to have authority to allocate physical resources to logical servers, but not have authority or capability to create administrative accounts on a logical server. A RM generally works to service requests from the SCM and does not instigate actions for itself or on other RM's.

Virtualization may enable complete separation between logical and physical servers so that a logical server may exist independent of a specific physical server. A logical server cloud virtualization may add a layer of abstraction and redirection between logical and physical servers. Logical servers may be implemented to exist as logical entities that are decoupled from any physical server resources that may have instantiated the logical server. Decoupling means that the logical attributes of a logical server are non-deterministically allocated to physical resources, thereby effectively creating a cloud of logical servers over one or more physical servers. This complete logical separation is facilitated by the addition of the SCM, which provides an automated multi-server management layer. An aspect to a logical server cloud involves the user not having to know or provide any physical server information to access one or more logical server(s), as this information is maintained within the SCM. Each logical server is substantially accessed in the same manner regardless of underlying physical servers, typically by using a predetermined uniform protocol. Thus, the user experiences no change in access approach even when a logical server is reallocated to a different physical server. Any such reallocation is thus completely transparent to the user.

The SCMs may further interface each other according to predetermined relationships or protocols, such as "peer" SCMs or server clouds or between a server cloud and a "super peer". The "super peer" may manage several "subclouds" in which an SCM interfaces or communicates with one or more logical and/or physical servers of another server cloud. The SCM of the server cloud operates as an intermediary or proxy for enabling communication between a logical server activated within a remote cloud. Logical servers may be moved from one server cloud to another or replicated between clouds. A remote SCM may manage one or more logical servers in a subcloud of a remote server cloud. In fact, a logical server may not be aware that it is in a remote cloud and may "think" that or otherwise behave as though it resides in the same cloud as the SCM managing its operations. The proxy functionality enables transparency between users and logical servers. The user of a logical server may or may not be aware of where the logical server exists or in which server cloud it is instantiated.

Many advantages and capabilities are enabled with cloud to cloud interfacing. Routing, switching, replication and cloud balancing may be performed between several different clouds, such as between "trusted" clouds, between "untrusted" clouds, or via an intermediary (e.g., another cloud, server, and/or shared storage) in which actions requested of one SCM are transparently performed by a different SCM. A "super peer" cloud may be established that has predetermined commercial relationships with other clouds or that is capable of querying public or otherwise accessible clouds for resource information. Such a "super peer" cloud may be established on a commercial basis, for example, to provide a free market exchange for servers or services related thereto. "Super peer" clouds may include intercloud proxy and predetermined business rules and relationships to conduct commercial transactions. Such commercial transactions may include, for example, sale or lease of logical servers on the market through a common exchange and medium, such as the Internet.

The present invention involves a system and method for the instant sharing of DNA date with privacy-preserving, high-performance and scalable DNA read mapping on hybrid clouds which include a public cloud and a private cloud. Such systems and methods may be implemented on computer hardware with appropriate software in the arrangements illustrated in FIGS. 1b and 1c, although many different arrangements and combinations of hardware and software may be used in accordance with the teachings of the present invention. Thus, these exemplary embodiments show possible implementations of the present invention and do not necessarily require all the components disclosed.

Figure 1B:
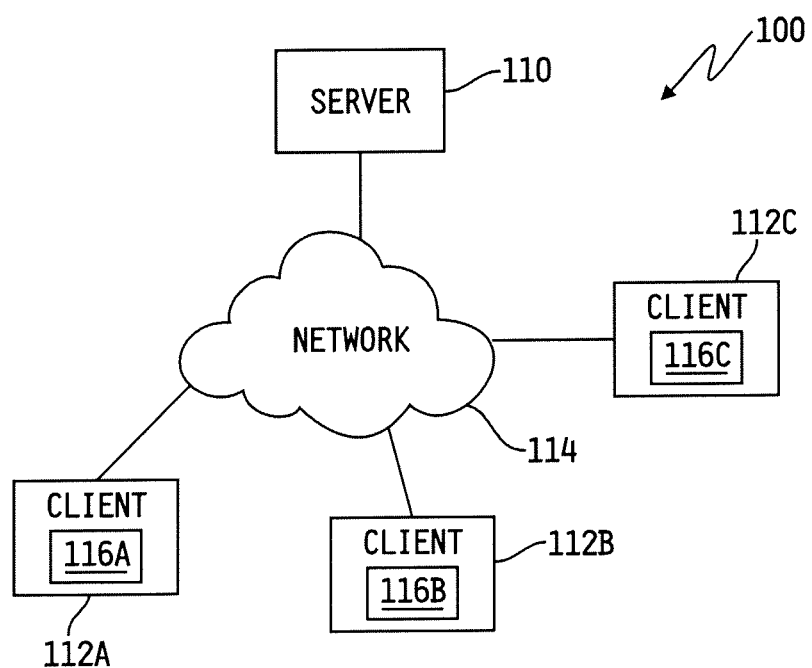
FIG. 1b is a schematic diagrammatic view of a network system in which embodiments of the present invention may be utilized.

FIG. 1b is a high-level block diagram of a computing environment 100 according to one embodiment. FIG. 1b illustrates server 110 and three clients 112 connected by network 114. Only three clients 112 are shown in FIG. 1 in order to simplify and clarify the description. Embodiments of the computing environment 100 may have thousands or millions of clients 112 connected to network 114, for example the Internet. Users (not shown) may operate software 116 on one of clients 112 to both send and receive messages network 114 via server 110 and its associated communications equipment and software (not shown).

Figure 1C:
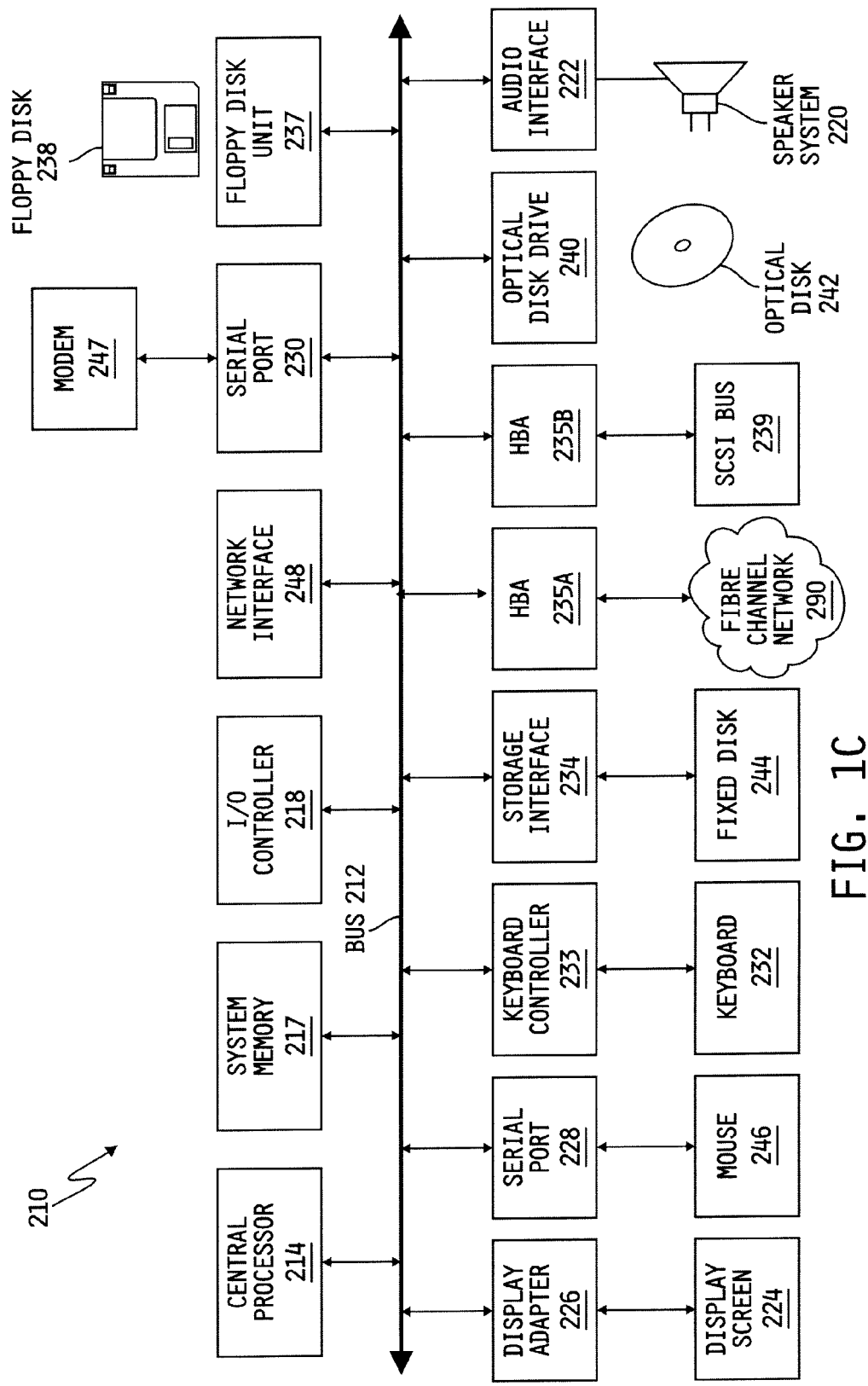
FIG. 1c is a block diagram of a computing system (either a server or client, or both, as appropriate), with optional input devices (e.g., keyboard, mouse, touch screen, etc.) and output devices, hardware, network connections, one or more processors, and memory/storage for data and modules, etc. which may be utilized in conjunction with embodiments of the present invention.

FIG. 1c depicts a block diagram of computer system 210 suitable for implementing server 110 or client 112. Computer system 210 includes bus 212 which interconnects major subsystems of computer system 210, such as central processor 214, system memory 217 (typically RAM, but which may also include ROM, flash RAM, or the like), input/output controller 218, external audio device, such as speaker system 220 via audio output interface 222, external device, such as display screen 224 via display adapter 226, serial ports 228 and 230, keyboard 232 (interfaced with keyboard controller 233), storage interface 234, disk drive 237 operative to receive floppy disk 238, host bus adapter (HBA) interface card 235A operative to connect with Fibre Channel network 290, host bus adapter (HBA) interface card 235B operative to connect to SCSI bus 239, and optical disk drive 240 operative to receive optical disk 242. Also included are mouse 246 (or other point-and-click device, coupled to bus 212 via serial port 228), modem 247 (coupled to bus 212 via serial port 230), and network interface 248 (coupled directly to bus 212).

Bus 212 allows data communication between central processor 214 and system memory 217, which may include read-only memory (ROM) or flash memory (neither shown), and random access memory (RAM) (not shown), as previously noted. RAM is generally the main memory into which operating system and application programs are loaded. ROM or flash memory may contain, among other software code, Basic Input-Output system (BIOS) which controls basic hardware operation such as interaction with peripheral components. Applications resident with computer system 210 are generally stored on and accessed via computer readable media, such as hard disk drives (e.g., fixed disk 244), optical drives (e.g., optical drive 240), floppy disk unit 237, or other storage medium. Additionally, applications may be in the form of electronic signals modulated in accordance with the application and data communication technology when accessed via network modem 247 or interface 248 or other telecommunications equipment (not shown).

Storage interface 234, as with other storage interfaces of computer system 210, may connect to standard computer readable media for storage and/or retrieval of information, such as fixed disk drive 244. Fixed disk drive 244 may be part of computer system 210 or may be separate and accessed through other interface systems. Modem 247 may provide direct connection to remote servers via telephone link or the Internet via an internet service provider (ISP) (not shown). Network interface 248 may provide direct connection to remote servers via direct network link to the Internet via a POP (point of presence). Network interface 248 may provide such connection using wireless techniques, including digital cellular telephone connection, Cellular Digital Packet Data (CDPD) connection, digital satellite data connection or the like.

Figure 2:
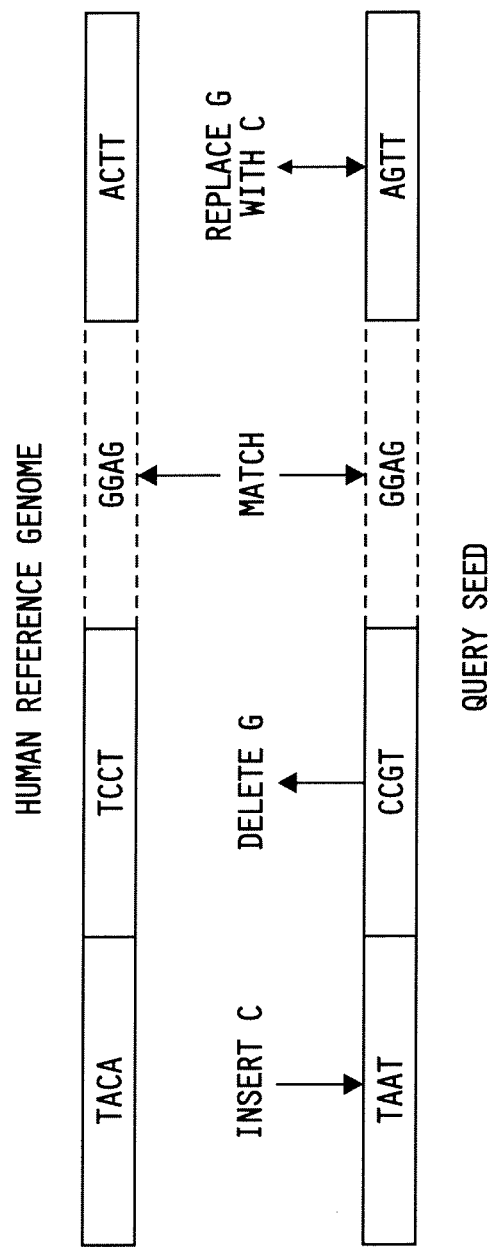
FIG. 2 is a schematic illustration depicting matching of DNA sequence read seeds with a reference genome on a public computing environment.

Many other devices or subsystems (not shown) may be connected in a similar manner (e.g., document scanners, digital cameras and so on). Conversely, all of the devices shown in FIG. 2 need not be present to practice the present disclosure. Devices and subsystems may be interconnected in different ways from that shown in FIG. 2. Operation of a computer system such as that shown in FIG. 2 is readily known in the art and is not discussed in detail in this application. Software source and/or object codes to implement the present disclosure may be stored in computer-readable storage media such as one or more of system memory 217, fixed disk 244, optical disk 242, or floppy disk 238. The operating system provided on computer system 210 may be a variety or version of either MS-DOS® (MS-DOS is a registered trademark of Microsoft Corporation of Redmond, Wash.), WINDOWS® (WINDOWS is a registered trademark of Microsoft Corporation of Redmond, Wash.), OS/2® (OS/2 is a registered trademark of International Business Machines Corporation of Armonk, N.Y.), UNIX® (UNIX is a registered trademark of X/Open Company Limited of Reading, United Kingdom), Linux® (Linux is a registered trademark of Linus Torvalds of Portland, Oreg.), or other known or developed operating system.

Moreover, regarding the signals described herein, those skilled in the art recognize that a signal may be directly transmitted from a first block to a second block, or a signal may be modified (e.g., amplified, attenuated, delayed, latched, buffered, inverted, filtered, or otherwise modified) between blocks. Although the signals of the above described embodiments are characterized as transmitted from one block to the next, other embodiments of the present disclosure may include modified signals in place of such directly transmitted signals as long as the informational and/or functional aspect of the signal is transmitted between blocks. To some extent, a signal input at a second block may be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

Turning now to the DNA data handling aspects of the present invention, the DNA data produced by next generation DNA sequencers consists of millions of reads, each typically including 30-120 nucleotides. These reads are randomly sampled from and aligned with a reference genome. To interpret them, the genetic locations of the reads must be found, which is achieved through read mapping. Given a set of reads, a reference genome and a threshold, the mapping operation aims at aligning each read to a substring on the reference genome such that the edit distance between the read and the substring does not exceed the threshold. This operation positions each read to its genetic location on the genome, which is necessary for most human DNA analyses, including SNP discovery, genotyping, gene expression profiling (e.g. RNA-seq), comparative genomics, personal genomics and others. It is also a critical step for analyzing the DNA data that belongs to human microbes, serving to sanitize such data by removing the DNA contamination from human hosts.

Serious threats to human genomic data include the identification of the individual from which the DNA comes. Such data is often produced from donors of clinic studies who, once identified could be linked to the disease or incur other serious consequences such as denial of access to health/life insurance, education, and employment. The Health Insurance Portability and Accountability Act (HIPAA) requires removal of explicit identifiers (such as name, social security number, etc.) before health data may be released. This protection, however, has been found to be insufficient for identification security of genomic data, because re-identification may occur through examining the genetic markers related to the donor's observable features (i.e., phenotypes) after the genetic locations of reads are recovered.

One genetic variation, widely-used for donor identification, is single-nucleotide polymorphism (SNP). SNPs occur when a single nucleotide (A, T, C or G) differs between the members of a species. It may take one of two alleles, either 0 (major) or I (minor). This variation has been employed by all existing re-identification techniques. Theoretically, other variations, such as rare alleles and copy number variation, may also be used to identify an individual, although these techniques face barriers given non-SNP variations are typically not mapped at the whole genome scale in any reference population.

Outsourcing the read mapping computations to low-cost commercial clouds, for example to Amazon Elastic Compute Cloud (EC2), is desired for processing terabytes of data at a low price (as low as 0.1 dollar per CPU hour). Because of the serious privacy risks associated with read mapping on cloud computing (e.g. identification of donor sequences and possible denial to access to health/life/disability insurance and educational/employment opportunities), commercial cloud providers cannot offer identification security assurance. To protect the sequence donors and avoid legal troubles, the National Institutes of Health (NIH) has thus far disallowed any datasets involving human DNA to be stored in or accessed by the public cloud.

Secure computation outsourcing (SCO) was one approach aimed a solving this problem. However, SCO approaches have not been able to enable secure read mapping on a commercial cloud. Particularly, SCO techniques like homomorphic encryption, secret sharing and secure multi-party computation (SMC) are too heavy weight to sustain a data intensive computation involving terabytes of data. For example, a privacy-preserving protocol proposed in prior research takes 3 minutes to calculate the edit distance between two 25-element sequences through homomorphic encryption and oblivious transfers. The same task may be performed somewhat more efficiently by an optimized SMC technique which, however, still needs 4.26 seconds and generates 4.38 megabytes of network traffic. Other SCO secret-sharing based approaches all require an immense amount of data exchanged between different share holders during a computation, and are therefore hard to scale. In addition, secret sharing does not prevent share holders from colluding which presents serious identification security issues.

Another approach aimed at protecting sequence donors with cloud computing (for DNA sequence analysis) was anonymizing the sequence data by aggregating reads from multiple individuals or by adding noise to reads. This is possible because a single read typically does not contain enough information for identifying its donor, and by mixing the reads from different parties, it becomes more difficult for the adversary to link those from the same person together. Although promising, various statistical techniques are effective at identifying donor individuals from the data. Further, aggregate and/or noisy read data is also susceptible to identification attacks.

The above-described generic approaches all fail to appreciate the special properties of this problem. The present disclosure, however, actually leverages these properties to build a solution. For example, the edit distance considered in read mapping is small, typically no more than 6 for standard 100-bp reads because human genetic variation is relatively small (below 0.3%). In practice, the differences between a read and its counterpart on the reference genome mainly comes from sequencing errors whose rate is typically about 2-3%. Therefore, a privacy-preserving technique that works on small edit distances should be enough for handling most sequence-analysis tasks.

The cloud also has distinctive features which the present disclosure leverages in building a solution. Cloud computing is extremely good at performing simple operations over a large amount of data. In practice, cloud computing often acts as a receiving end of the computation "spill-over" from an organization's internal system when its computing resources are about to deplete. This way of computing, which involves both the private cloud within an organization and the public commercial cloud, is called hybrid cloud computing. Hybrid cloud computing has already been adopted by most organizational cloud users and is still undergoing rapid development. As described herein, hybrid could computing may be used for secure outsourcing of computation tasks to untrusted environments by splitting a task such that a large amount of relatively simple computation over encrypted data (like secure string matching), while a user's private cloud works on a small amount of relatively complicated computation such as calculating edit distances.

The present disclosure shows how the aforementioned features may be leveraged to enable read mapping, one of the most important and pervasive operations in DNA sequence analyses, to be securely and practically executed on the hybrid cloud. The new methods disclosed and described herein are based upon a seed-and-extend strategy, which first matches a seed a segment of a read with one (d+1)th of the read's length given an edit distance d, to substrings on the reference genome and then extends from these substrings to align the whole read with the reference genome. The methods of the present disclosure split the mapping task along these two stages, delegating them to public and private clouds respectively. As explained herein, the public cloud searches for the exact matches between the keyed hash values of seeds and substrings (called l-mers for a substring of length l) on the reference genome to determine the possible positions of reads, while the private cloud extends from these positions to find the optimal alignments of these reads.

While a single extension operation (involving calculation of an edit distance under a threshold) may be efficient (in linear time), read-mapping is typically burdened by a huge number of extensions that need to be made. Therefore, it is conceivable that once the seeding process yields only a few (or even unique) positions for each read, the workload of the extension stage which is undertaken by the private cloud may become much lower than that of the public cloud. However, with traditional seed-and-extend approaches, this is not the case (particularly when the seed is too short) due to a relatively large edit distance (e.g., 6 for 100-bp). To address these challenges, the present disclosure provides a system and method which utilizes seed combinations such that a small number of extensions for each read, at a spatial overhead that may be easily afforded by today's clouds, is ensured.

According to the system and method of the present disclosure enabling read mapping on the public cloud includes either encrypting the data or anonymizing it, making it unidentifiable. However, only a few cryptographic approaches support secure calculation of edit distances, and they are too expensive to sustain a data-intensive computation involving terabytes of data (see, for example, Example 2.4). Less clear is the efficacy of simple data anonymization techniques such as aggregation, noise adding, and data partition. These techniques have previously been used to protect the privacy of genomic data. As an example, Genome-Wide Association Studies (GWAS) use DNA microarrays to profile a set of pre-determined SNPs from a group of patients (called case) in order to study the genetic traits of their common disease. The SNPs from different case individuals were aggregated into a mixture, from which nothing but the counts (or equivalently, the frequencies) of different SNP values (alleles) may be observed and used for statistical analysis. However, if released to a public environment, data is vulnerable to re-identification attacks because allele frequencies of a reference population may be acquired from public sources such as the International HapMap Project, a DNA sample from an individual and the individual's presence in the case population may be determined from the aggregate data through a statistical test.

Different from the microarray data studied in the prior work, the SNP sets covered by the reads from two persons often differ significantly due to the randomness in sequencing. However, as described herein anonymization techniques on read data is also vulnerable to re-identification attacks. For example, and further disclosed and exemplified herein, to ensure that no more than 10% of a case group might be identified at a confidence of 0.99, reads from about 38,000 individuals with 1 million reads each needs to be aggregated.

FIG. 1a presents a high-level design of an exemplary embodiment of the system and method disclosed herein. According to the present disclosure, a hybrid cloud is utilized with public commercial cloud delegated the computation over encrypted read datasets, and a private cloud directly working on the data. The disclosed system and method allows a private cloud to undertake a small amount of the workload to reduce the complexity of the computation that needs to be performed on the encrypted data, while still having the public cloud shoulder the major portion of a mapping task. Further, and to this end, tasks are divided according to the seed-and-extend strategy. The seeding part is to roughly locate a read on the reference genome by matching a small segment of it to the substrings on the genome. For example, given an edit distance of 3 and reads of 100 bps, the system and method of the instant disclosure may partition each read into 4 segments (seeds), each of 25 bps. At least one of these seeds will match a 25-mer on the read's counterpart on the reference genome. Searching for this position may be done over the keyed-hash values of the seeds and 25-mers. The system may use a secret key and a cryptographic hash function to fingerprint all unique 25-mers on the reference genome and save their hash values to the public cloud, and then compare the hash values of the seeds with them. Accordingly, all the matches found thereby are reported to the private cloud, which extends the reads from the positions indicated by these matches to find an optimal alignment for each read using a fast threshold-based edit-distance algorithm as disclosed and described herein.

The system and method presented herein provides surprisingly effective results. The majority of 25-mers are unique on the genome, and as a result, a 25-bp seed may often locate a read at a small set of positions, which reduces the workload of calculating edit distances between millions of reads and billions of reference 25-mers to the extensions that just need to happen at millions of positions. However, when the seed becomes too short, random matches occur, which increases the extension workload. By way of example, given an edit distance of 6, the seed for a 100-bp read has only 14 bps and often matches hundreds of positions. The disclosed system resolves this problem by using a novel design that performs the seeding over the keyed-hash values for 2-combinations of 12-bp seeds, which thereby significantly reduces the workload of the private cloud at a spatial overhead that may be easily afforded by the modern clouds (see the discussion of the use of multiple seeds below).

The privacy assurance of the present system and method may be evaluated by the amount of information the public cloud may infer from the data it observes. To achieve an ultrafast mapping, the instant system may adopt a keyed hash allowing the public cloud to unilaterally determine whether a match happens. This may cause a concern about a frequency analysis inferring with the content of l-mers by counting the matches their hashes receive. Initial assessments of this risk further described below, utilizing a whole genome study, reveal that the re-identification power one may achieve through such a frequency analysis is very limited.

Additionally, the privacy assurance of the disclosed system and method is considered and described herein from the perspective of an adversary who aims at re-identifying the individuals related to read data. As discussed before, this re-identification is a privacy concern for releasing protected health information (such as reads) on a public environment, such as a commercial cloud, and therefore a major barrier to moving read mapping to the public cloud. Privacy assurance models disclosed herein assume that the adversary has a DNA sample of a testee, the person she wants to identify from a read dataset, and a reference population genetically similar to those whose reads are inside the dataset. Access to such background knowledge is widely considered to be a very strong assumption that gives the adversary advantages in re-identification. Also, an adversary could compromise the nodes on the public cloud and control their operations. If this happens, the computation these nodes perform may fail, but such a circumstance will likely not affect the adversary's ability to acquire sufficient information to identify read donors.

As previously discussed herein, a prominent feature of read mapping is that the edit distance is small between a read and the reference substring it should be aligned to. Since the genetic variation between different humans is typically below 0.3% and sequencing errors are about 2-3%, almost all the mapping tasks look at a distance threshold no more than 6 for standard 100-bp reads. For such a small edit distance, alignments may be efficiently found through seed-and-extend, a method that has been extensively used in high-performance mapping systems like BLAST, BLAT, Bowtie, RMAP and Cloud-Burst. The system and method disclosed herein is based upon the observation that for a sequencing read partitioned into d+1 segments (seeds) of length l, if it has at most d errors, then at least one of its d+1 segments matches a substring within the region on a reference genome the read should be mapped onto. As such, the current system disclosed herein uses the segment to roughly locate the read on the reference (the seeding stage), and then extend from these possible locations to determine where it belongs (the extension stage). FIG. 2 presents an exemplary embodiment of the disclosed system and method having at least one of the 4 4-bp seeds of a 16-bp read match a 4-mer within a 16-mer whose edit distance from the read is 3. The system and method disclosed herein utilizes the public cloud to take care of the seeding, roughly locating reads, thereby enabling the private cloud to quickly extend each read at a very small set of positions. Note that such an extension may be done by a linear algorithm that calculates the edit distances no more than a threshold.

To perform the seeding on the public cloud, the keyed hash values for both the reference genome and individual seeds are computed. Specifically, given a keyed hash function $H_K(\ )$ with a secret key K, the instant method first fingerprints all the unique l-mers $\alpha_i$ on the reference genome: $H_K(\alpha_1)$, $H_K(\alpha_2)$ . . . and then sends their hash values to the public cloud. Unique l-mers make a frequency analysis more difficult to succeed in re-identification. Depending on the length l, l-mers have different levels of repetitions on a human genome. For example, it was found that more than 80% of 24-mers are unique on the reference genome. When arranged in a random order, they hide their position information. Additionally, keyed hashes for the seeds $s_j$, extracted from m reads are also computed: $H_K(s_1), H_K(s_2), \ldots H_K(s_{(d+1)m})$, this list is randomly permutated and then delivered to the public cloud for the seeding operation. The present system and method disclosed herein, in one embodiment, adopts Secure Hash Algorithm 1 (SHA-1) and a 256-bit secret key and only uses the first 10 bytes of an l-mer's hash as its fingerprint for the comparison. The rest bytes are XORed with the information for locating the l-mer on the reference genome. In alternative embodiments of the invention, SHA-1 may be replaced with the SHA-0 or SHA-2 methods, or any other suitable cryptographic hash function, for example GOST, HAVAL, MD2, MD4, MD5, PANAMA, RadioGatún, RIPEMD, RIPEMD-128/256, RIPEMD-160/320, SHA-256/224, SHA-512/384, Tiger(2)-192/160/128, or WHIRLPOOL.

The seeding task delegated to the public cloud, in the methods disclosed herein, is as simple as comparing all the hashes of the seeds with those of the reference l-mers and reporting the indices of the matched sequence pairs (i, j) to the private cloud. However, one concern presented is the scale of such a computation, which involves millions upon billions of string comparisons. According to an exemplary embodiment of the instant disclosure fast seeding may be achieved by building an index for the reference genome (as done by some fast-mapping software systems such as Bowtie. This approach, however, requires a huge amount of memory, and therefore cannot be easily parallelized. Another exemplary embodiment of the present disclosure involves ultrafast sorting being performed in a computing cloud to do the seeding. Specifically in this embodiment, the public cloud pre-sorts the l-mers according to their hash values. For every batch of seed hashes, the cloud first sorts them and then merges them with the sorted l-mer hashes to find matches. The public cloud may support high-performance sorting. For example, Terasort which runs on Hadoop has been reported to attain a sorting speed of 0.578 terabytes per minute.

The private cloud extends the seeds at the locations where matches happen. These locations are recovered from the indices of seed hashes and the l-mer hashes they match, as reported by the public cloud. For this purpose, two look-up tables are needed: one maps a reference l-mer to its occurrences on the reference genome, and the other maps a seed to the read it belongs to. In general, the first table is large, at least 60 GB, and often cannot be completely loaded into the memory. Random access to this table from the hard drive will cause a significant delay. The system disclosed herein is based upon the features of human genomes. When l goes above 20, most l-mers are unique across the reference genome. Particularly, only a small portion (below 20%) of 24, 25-mers repeat. For every unique l-mer $\alpha_i$, the disclosed method keeps its location information directly on the last 6 bytes of $H_K(\alpha_i)$, Specifically, let $\theta_i$ be these bytes. XOR the location of $\alpha_i$, $L_i$, onto $\theta_i$: $\pi_i = \theta_i \_ (I_i || L_i)$, where $l_i$ is a one-byte indicator for the uniqueness of the l-mer. Once this l-mer is matched by a seed (that is, the first 10 bytes of the seed's hash matching the first 10 bytes on the l-mer's hash), $L_i$, is recovered from $\pi_i$ using $\theta_i$ which is kept on the private cloud. For those still in the table, the system may organize them according to the indices of their hashes to ensure that only sequential access happens when searching the table.

When the read dataset is relatively small (50 million reads or less), its look-up table, which does not go above 1.2 GB, may often be accommodated in the memory. In the table, the system also keeps the last 6 bytes of seed hashes for decrypting the location information of the l-mers they matched. To handle a large dataset, the disclosed approach encrypts the read information $R_j$, for a seed $s_j$ using a simple stream cipher such as Advanced Encryption Standard (AES) Counter (CTR). Specifically, the instant method first computes the key-stream $E_K(V||j)$, where V is an initial vector and K' is another secret key, and then uses the first 10 bytes of the stream $\sigma_j$ to do the encryption: $\tau_1 = \sigma_j \theta(R_j || \theta_j)$, where $\theta$, is the last 6 bytes of $H_K(s_j)$. This cipher text is concatenated with the first 10 bytes of the seed's hash, and given to the public cloud. Once the cloud finds a match between the hashes of $\alpha_i$, and $s_j$, it sends $(\pi_i, \tau_j, j)$ to the private cloud for recovering $L_i$ and $R_j$. Other encryption cipher block modes of operation may be used in alternative embodiments of the invention, such as Message Authentication Code (MAC), Cipher Block Chaining Message Authentication Code (CBC-MAC), Cipher based MAC (CMAC), Keyed-Hash Message Authentication Code (HMAC), Galois/Counter Mode (GCM), Electronic CodeBook (ECB), Cipher-Block Chaining (CBC), Propagating Cipher-Block Chaining (PCBC), Cipher FeedBack (CFB), Output FeedBack (OFB), etc. In other embodiments of the invention, encryption methods such as Blowfish, DES, Triple DES, Serpent, Twofish, Camellia, CAST-128, IDEA, RC2, RC5, SEED, Skipjack, TEA, XTEA, 3-Way, Akelarre, Anubis, ARIA, BaseKing, BassOmatic, BATON, BEAR and LION, CAST-256, CIKS-1, CIPHERUNICORN-A, CIPHERUNICORN-E, CLEFIA, CMEA, Cobra, COCONUT98, Crab, Cryptomeria/C2, CRYPTON, CS-Cipher, DEAL, DES-X, DFC, E2, FEAL, FEA-M, FROG, G-DES, GOST, Grand Cm, Hasty Pudding cipher, Hierocrypt, ICE, NXT, Intel Cascade Cipher, Iraqi, KASUMI, KeeLoq, KHAZAD, Khufu and Khafre, KN-Cipher, Ladder-DES, Libelle, LOKI97, LOKI89/91, Lucifer, M6, M8, MacGuffin, Madryga, MAGENTA, MARS, Mercy, MESH, MISTY1, MMB, MULTI2, MultiSwap, New Data Seal, NewDES, Nimbus, NOEKEON, NUSH, PRESENT, Q, RC6, REDOC, Red Pike, S-1, SAFER, SAVILLE, SC2000, SHACAL, SHARK, SMS4, Spectr-H64, Square, SXAL/MBAL, Threefish, Treyfer, UES, Xenon, Xmx, XXTEA, Zodiac, etc.

The workload of the private cloud may be determined by the number of extensions it needs to perform for each read. As discussed before, when l is no smaller than 20, most l-mers are unique and thus the reads whose seeds match them only need to be extended a few times. Among the rest of l-mers that reoccur on the genome, some of them are actually part of longer repetitive substrings, and only need to be extended once for all these reoccurrences. This may be achieved by compressing the reference genome according to its 100-mers. The instant system may also identify all the unique 100-mers and extend the reads on them instead of the whole genome. Also important is the extension algorithm, which needs to be highly efficient. The system and method disclosed herein utilizes a threshold dynamic programming algorithm to compute the edit distance no more than a threshold d. This algorithm's complexity is only O (dλ), where λ is the length of the read, and is much more efficient than an algorithm that does not use the threshold, for example, whose complexity is O ($\lambda^2$).

The disclosed application of "seed-and-extend" works well when the seeds are at least 20 bps. Given standard 100-bp reads, this means that the edit distance should not go above 4. Research has shown that less than 20% of 20-mers re-occur, and as a result, on average about 10 extensions are required for a read to be aligned to a 100-mer within its distance threshold. Estimates of how the computing workload is split between the public and private clouds may therefore be determined. For example, consider a read dataset with 10 million reads. With an edit distance of 4, each read is broken into 5 seeds. The sorting performance the public cloud could achieve is m log m, where m is the number of the seeds. This amounts to roughly 12.8 billion comparison operations (comparing 2 bytes). Added to this overhead is the cost for merging the outcome with around 5 billion unique reference 20-mers (10 bytes each), which takes about 25 billion comparisons on average. Altogether, the public cloud need to do 37.8 billion comparisons. On the private cloud front, each read needs to be extended less than 10 times on average. Each extension works under the distance threshold of 4 and involves a read of 20 bytes, and thus needs about 80 comparisons. Therefore, the private cloud's computing task includes about 8 billion comparisons, roughly 17.5% of the overall workload. In other words, when the seed length is at least 20 bps, the disclosed system and method employs the public cloud to undertake at least 82.5% of the mapping computation. Note that in practice, the private cloud often does not need to extend all the reads, as some of them have no seeds that match any l-mers. A prominent example is the task of filtering out human reads in microbiome sequencing data, one of the most important applications of read mapping. In this case, typically far less than 10% of the reads will be extended, and therefore, the private cloud shoulders less than 2% of the computation.

To prepare for the mapping, the private cloud computes the keyed hashes for reference l-mers, which only needs to be done once, and seed hashes for every dataset. By way of example, using a high-end desktop (2.93 GHz Intel Xeon), it was found that SHA-1 achieved a throughput of 100 million l-mers per minute using a single core. In other words, a typical dataset with 10 million reads may be processed within a minute. Fingerprinting the whole reference genome took longer time, about 7 minutes using 10 cores. However, this only needs to be done once. Further, it should be noted that SHA-1 is not known for its speed. It was used in our implementation for the sake of simplicity. Many other cryptographic hash functions perform much better, and may be used as alternate embodiments of the invention.

When edit distance goes up to 5, the 6 16-bp seeds of a read often align it to hundreds of possible positions for extensions. To reduce the number of matches, the present system uses multiple seeds: given an edit distance d, the system may partition a read into d+2 seeds, of which at least 2 will have exact matches on the region the read should be aligned to. For example, a 100-bp read, once partitioned into 8 12-bp seeds, may use 2 seeds (totaling 24 bps long) to find out the 100-mers to which its distance may not exceed 6. Given the length of such combined seeds, most reads may be located at a few genomic positions. A straightforward implementation of this idea, however, will force the private cloud to intersect a large number of positions matched by the short seeds for each read. For the read using 12-bp seeds, thousands of matched positions need to be compared to find those on the same 100-mers.

The disclosed system and method also works for mapping 2-seed combinations by, again, building upon the special features of the cloud. Today's clouds are designed for data intensive computations, and may easily store and process terabytes of data at a low cost, as long as the operations on such data are simple and parallelizable. The disclosed system employs this property to convert the intersection operation to the string matching that happens between the keyed-hash values of 2-seed combinations and l-mer combinations. Specifically, for every 100-mer on the reference genome, the system saves to the public cloud the unique hashes of the 2-combinations of its l-mers $\alpha_i$: $H_k(\alpha_1\|\alpha_2), H_k(\alpha_1\|\alpha_3), \ldots, H_k(\alpha_1\|\alpha_3) \ldots, H_k(\alpha_{100-l}\|\alpha_{101-l})$. Given a read dataset, the private cloud also fingerprints all the 2-combinations of d+2 seeds$_{sj}$ for each read: $H_k(s_1\|s_2), \ldots, H_k(S_d+1\|S_d+2)$. These combined-seed hashes are compared to those of the l-mer combinations on the public cloud to help locate the reads on the reference genome.

Figure 3:
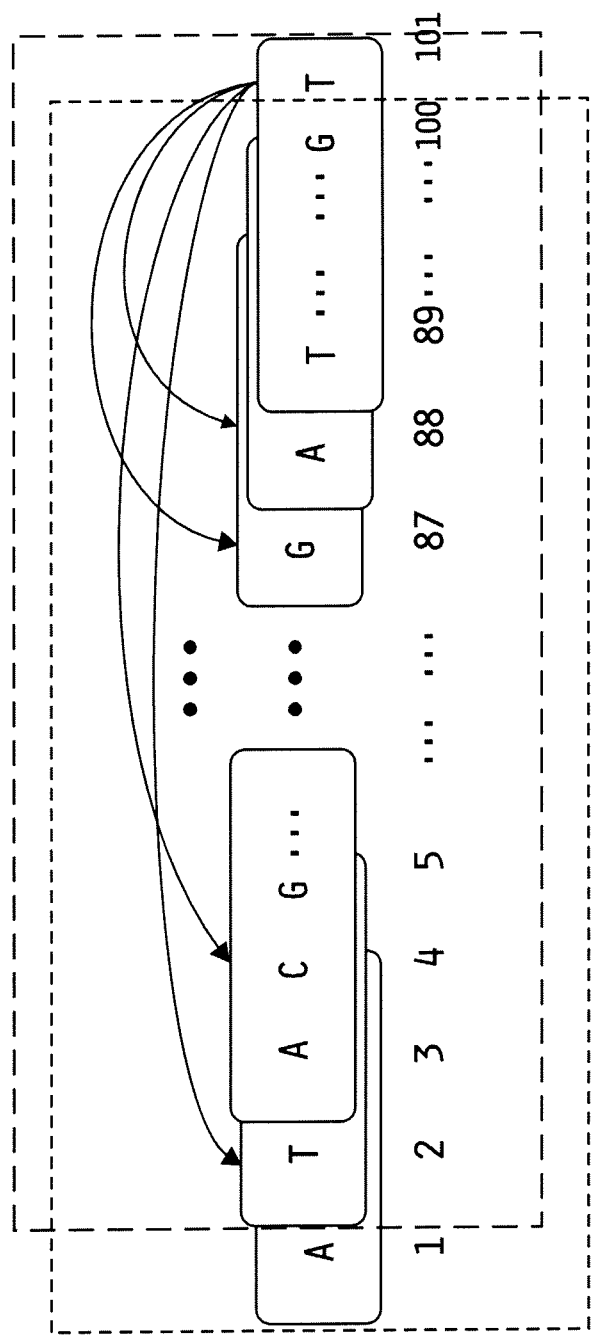
FIG. 3 is a schematic illustration depicting simultaneous matching of two DNA sequence read seeds within a given segment of a reference genome on a public computing environment.

To perform this seeding operation, the public cloud needs to accommodate the keyed hashes for both reference l-mer combinations and combined seeds. Each 100-mer contains 101-l different l-mers and totaling [(101-l) (100-l)]/2 combinations. For example, there are 3,916 combinations of 12-mers within a 100-bp window. However, the total size of the reference genome will not grow that much, as the seeds within two overlapping 100-mers are also heavily overlapped. Referring to FIG. 3, whenever the window right shift by one bp, only one new l-mer has been created, which brings in an additional 100-l combinations. Therefore, the total size of the reference genome actually increases by roughly 100-l times. In the above example, 12-mer combinations are about 88 times the total size of all reference 12-mers. Using the 16 bytes of the 20-byte output of SHA-1, the keyed hashes for the reference sequences have about 5.32 TB. This amount of data may be accommodated by the clouds. For example, to keep such data at EC2, the cost to NTH is about $680 per month. Operations on this reference include sorting and merging with the combined seeds, which may also be efficiently done through ultrafast sorting algorithms. The combined seeds only cause moderate rise in the spatial cost: the number of 2-combinations of d+2 seeds is [(d+1)(d+2)]/2, just (d+1)/2 times the size of the seeds. For example, the 12-bp seed combinations on 100-bp reads are just 4 times the size of the original dataset; the keyed hash data of 10 million such reads has about 2.8 GB.

The private cloud computes the hashes and delivers them to the public cloud for each mapping task. Given merely (d+1)/2 times the increase in the size of the data, the overheads of such a preparation are completely acceptable. Since the combined seeds often are sufficiently long (>20 bps), they may pin a read down to a very small set of extension locations. By way of as an example, research has shown that nearly 70% of combined 12-mers (24 bps long) are unique across the human genome. Acting on the outcomes of the seeding performed upon these combinations, it was found and is discussed herein, that each read should be extended for about 30 times on average, even when the reference genome has not been compressed according to its 100-mers. To further avoid unnecessary extensions, the disclosed system and method uses a strategy that for each read, first extends the combined seed with a unique match. This works particularly well for the task like microbiome filtering, which stops to remove a read as soon as it is found similar to a human 100-mer. A challenge in regard to the private cloud involves the sizes of the look-up tables. The table for finding reads (from the combined seeds) remains okay, and may be replaced with the encoding technique as further described herein. The other table, which maps l-mer combinations to their positions on the reference genome, however, needs to be expanded by nearly 100 fold, and has a size of roughly 400 GB. Therefore, to utilize this table efficiently, it may be partitioned into a set of sub-tables and distributed to multiple nodes on the private cloud. As discussed herein, the content of the original table is organized according to the index order of the hashes for l-mer combinations on the public cloud, for the purpose of sequential data access from the hard drive. Further, the public cloud groups the matches it finds into several bins with regard to the index ranges of the sub-tables, and then dispatch these bins to different nodes for distributed table look-ups and extensions on the private cloud.

Using combined seeds, the computing burden of intersecting the matches produced by short seeds is essentially outsourced to the public cloud, which further reduces the proportion of the overall workload the private cloud needs to undertake. For example, consider a dataset of 10 million reads and a distance of 6. In this exemplary embodiment, there are 28 combined 12-bp seeds for each read. Sorting the keyed hashes for these 280 million combined seeds incurs about 78.5 billion comparison operations. To merge the sorted list with that of the hashes for 12-mer combinations, which include about 400 billion 10-byte sequences, the public cloud needs to perform about 2078.5 billion comparisons on average. On the private-cloud front, each read needs to be extended roughly 30 times on average. Each extension processes about 19 bytes of the read with a distance threshold of 6. Altogether, the computational overheads of the extensions are roughly 34.2 billion comparisons, just 2% of the whole mapping workload. Thus, the present system and method works well even when/drops to 10. That is, it may support secure computation of edit distances up to 8 for standard 100-bp reads. Thus, the present system and method provides more than enough for almost all the read mapping and analysis tasks.

Further, the one-time fingerprinting of all 12-mer combinations using SHA-1 takes about 7 hours with 10 cores (2.93 GHz Intel Xeon). The 280 million seeds for the 10 million reads only need about 3 minutes to hash. The AES CTR and SHA-1 methodologies described herein may be replaced with any other suitable deterministic encryption schemes, like block ciphers in electronic codebook mode (ECB) or counter mode (CTR), for example Rivest Cipher (RC5), Twofish, the Carlisle Adams and Stafford Tavares algorithm (CAST-256), etc. And they may also be replaced with any other keyed hash schemes (including all kinds of deterministic message authentication code) based upon suitable cryptographic hash functions like Message-Digest Algorithm (MD5), SHA-1, SHA-2, BLAKE, etc.

According to the present system and method, only keyed hash values of seeds and l-mers are exposed to the public cloud, from which the adversary cannot directly recover reads. The system further ensures that only the hashes of unique l-mers are disclosed, making them hard to distinguish by an observer. Under such protection, the most useful information available to the public cloud is just the counts of the exact matches that individual reference hashes (those of l-mers or combinations) receive from the hashes of seeds or combined seeds. Therefore, the adversary's best chance is leveraging such information and the background knowledge at the adversary's disposal (i.e., the genomes of a reference population and a DNA sample from the testee) in an attempt to determine the presence of the testee's DNA in the read dataset which the adversary cannot directly access. Note that an assumption of an adversary having such background knowledge strongly favors the adversary as this knowledge cannot easily be obtained. As such, a threat from this perspective is further analyzed herein.

As discussed above, the public cloud may only observe the frequency with which the keyed hash value of each l-mer has been matched. Such a frequency reflects the extent to which each l-mer re-occurs on the human genome, and when SNPs are involved, is also affected by their allele frequencies across a population. This observation allows the adversary to categorize the keyed hash values of l-mers into h bins $B_1, \ldots B_h$: all those within the same bin have the same frequencies and therefore cannot be distinguished from each other, while those in different bins may be differentiated. Should the adversary manage to link each bin to a set of l-mers on the reference genome. The following describes the adversary's options.

Let $f_k$ be the frequency with which all hash values within the bin $B_k$ appear in a seed-hash dataset and $F_k$ be the frequency of all l-mers in that bin across a reference population (e.g., the HapMap population). Consider the situation when the adversary manages to acquire a DNA sample from an individual (the testee), and therefore may find out the frequency$_{pk}$ of the l-mers in that bin. The adversary's objective is to determine whether the testee is present in the case group (i.e., whether her sequencing reads are included in the read dataset being mapped). This may be done using the following statistic:

$$\bar{D} = \sum_{k=1}^{h} \bar{D}_k = \sum_k [|\rho_k - F_k| - |\rho_k - \bar{f}_k|]. \quad \text{(Equation 1)}$$

D is called Homer-like test herein. It is a direct application of Homer's test, which works on the allele frequencies of SNPs, to the re-identification over the frequencies of hashed l-mers in different bins. This test is shown to be close to optimal in re-identifying the testee from the case group given the background knowledge about the reference population and the testee's DNA sample. Another near-optimal test is the log likelihood ratio test, which is known to be optimal when the occurrences of the l-mers in different bins are completely independent from each other. It is also found to be extremely effective in determining the presence of an individual's DNA in an aggregated dataset. This statistic is described by the following equation:

$$\bar{T} = \sum_{k=1}^{h} \bar{T}_k = \sum_k [\log(Pr_k^C(\rho_k)) - \log(Pr_k^R(\rho_k))]. \quad \text{(Equation 2)}$$

Let $\bar{p}_k^C$ be the frequency of all l-mers in $B_k$ from a case individual's genome, and $\bar{p}_k^R$ be the corresponding l-mers frequency from a reference individual. Given $p_k$ derived from the testee's genome, in Equation 2, $Pr_k^C(p_k)$ (for the case group) and $Pr_k^R(p_k)$ (for the reference group) represent the cumulative probabilities of observing the frequency of $B_k$ members from any individual's genome that is more deviated from the expected values of $\bar{p}_k^C$ and $\bar{p}_k^R$ than $p_k$ respectively. These cumulative probabilities are calculated based upon the distribution of $\bar{p}_k^C$ in the case group, denoted by $p_k^R(\ )$, and that of $\bar{p}_k^R$ in the reference group, denoted by $P_k^C(\ )$. According to the present disclosure, both distributions were modeled by a normal distribution: $P_k(x) \sim n(\mu_k, \sigma_k)$, where, $\mu_k$ and $\sigma_k$ were approximated by the mean and standard deviation of the numbers of l-mers in $B_k$ across all individuals in the case or reference group. Since these two cumulative probabilities are calculated in the same way, $Pr_k(p_k)$ is used to describe this calculation, as follows:

$$Pr_k(\rho_k) = \begin{cases} P_k(x \le \rho_k) & \text{if } x \ge \mu_k \\ P_k(x > \rho_k) & \text{if } x < \mu_k. \end{cases} \quad \text{(Equation 3)}$$

Given the aforementioned background knowledge, the above two test statistics, which are both near optimal, are the most powerful identification tools available to the adversary (if the correlation among l-mers, discuss later, is not considered). The present disclosure evaluates the identification powers of these statistics based upon real DNA data from the largest population available in the public domain. The whole reference genome was compressed into 372,869,332 unique 24-mers that involve SNPs. This analysis focuses on SNPs, as for the time being, other variations cannot be effectively leveraged for re-identification during read mapping. The selected 24-mers were further classified into 7,260,607 bins. For simplicity, this was done in a pessimistic way, which further gives the advantage to the adversary. Specifically, the 24-mers involving a single SNP were grouped into bins according to their frequencies, which depend not only on their rates of reoccurrences across the reference genome but also on the allele frequencies (with 2 digits of precision) of the SNPs they carry. For those associated with more than one SNP, a unique bin was created for each of them, assuming that they were identified by the adversary. Without considering the correlation among the 24-mers, this is the best the adversary may do.

The reference individuals were simulated from the reference human genome. To produce realistic human genome sequences, the SNP sites on the reference genome were randomly flipped according to their allele frequencies reported by the HapMap. $\bar{F}_k$ in the Homer-like test (Equation 1) and $P_k^R(\ )$ in the likelihood ratio test (Equation 2) were estimated from 100 simulated human genome sequences, which constituted the reference group. The YRI population on the HapMap (the largest population whose DNA data is available in the public domain) was used to construct a case group and a test group (a population including neither case nor reference individuals). Each of these two groups had about 40 individuals. Then, 10 million reads from each individual in the case group was sampled to compute the frequency of Bk across the case population ($\bar{f}_k$), and the frequency over the individual's genome ($\bar{p}_k^C$) and its distribution ($P_k^C$) over the case population. After that, for each case and test individual, the likelihood of their presence in the case group was tested through the Homer-like test D (Equation 1) and the likelihood ratio test T (Equation 2) using their frequencies pk for individual B.

Figure 4A:
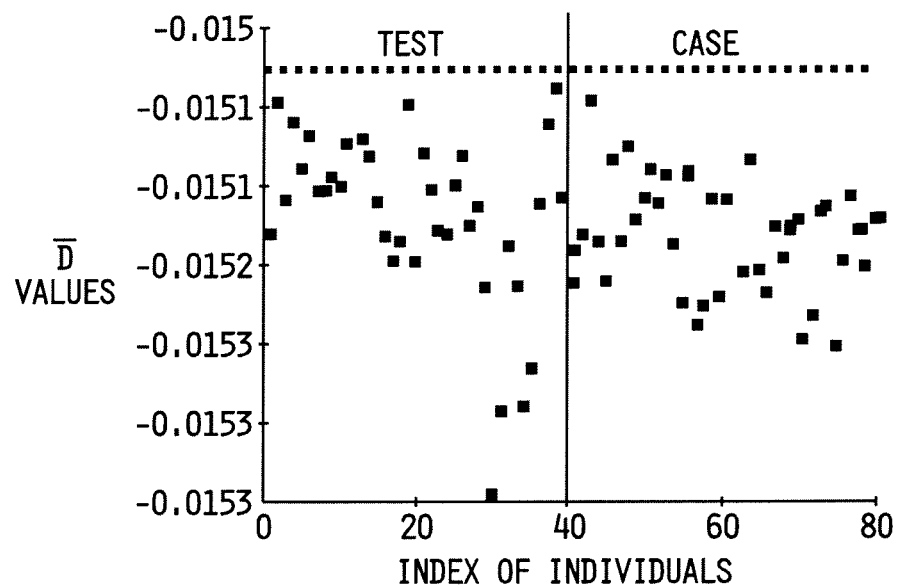
FIG. 4a is a graph illustrating the power of the Homer-like statistic test and the likelihood ratio test in an experiment evaluating the re-identification powers of an adversary for distinguishing individuals from case and test groups.
Figure 4B:
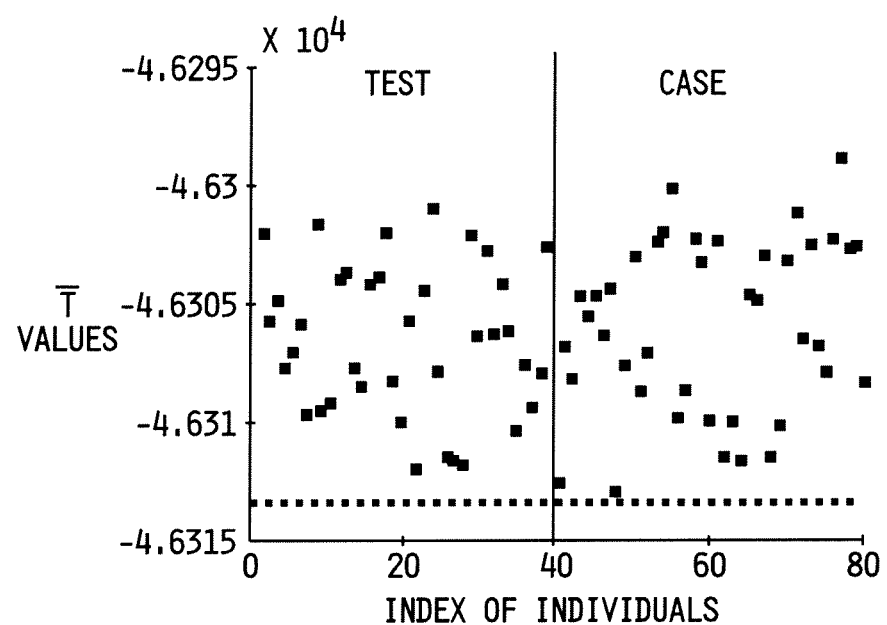
FIG. 4b is another graph illustrating the power of the Homer-like statistic test and the likelihood ratio test in an experiment evaluating the re-identification powers of an adversary for distinguishing individuals from case and test groups.

Eighty YRI individuals were randomly sampled from in order to form the case and the test groups, and the re-identification powers the adversary may achieve over them was evaluated. This experiment was repeated 40 times, and it was found that each time the case and the test individuals were completely indistinguishable from each others. FIGS. 4a and 4b present examples, illustrating the power of the Homer-like statistic test and the likelihood ratio test in one experiment. The distributions of D and T are completely indistinguishable between the case and test groups. For D, at 1% false positive rate level (denoted by the dash line), one individual in the case group and one in the test group (i.e., a false positive) were identified (above that line), indicating equal true positive and false positive rates, and thus no statistical power is achieved. For T, only a test individual was identified (below the dash line).

Figure 4C:
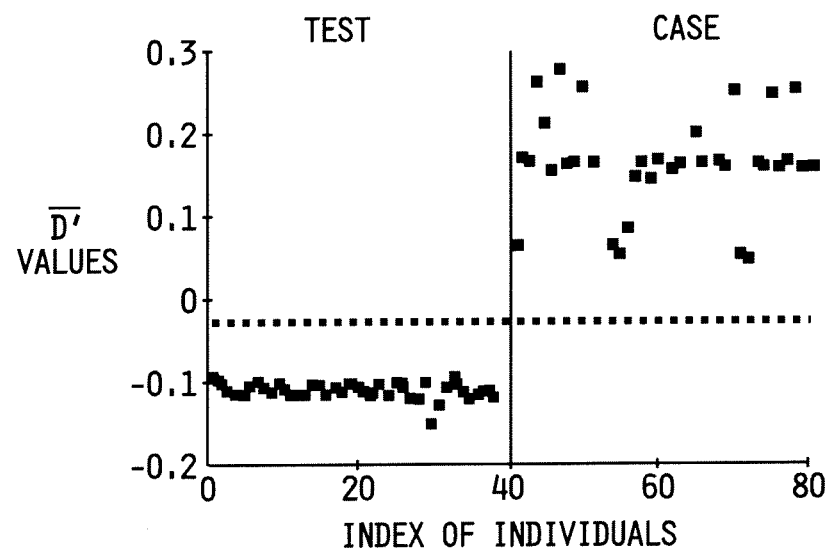
FIG. 4c is yet another graph illustrating the power of the Homer-like statistic test and the likelihood ratio test in an experiment evaluating the re-identification powers of an adversary for distinguishing individuals from case and test groups.
Figure 4D:
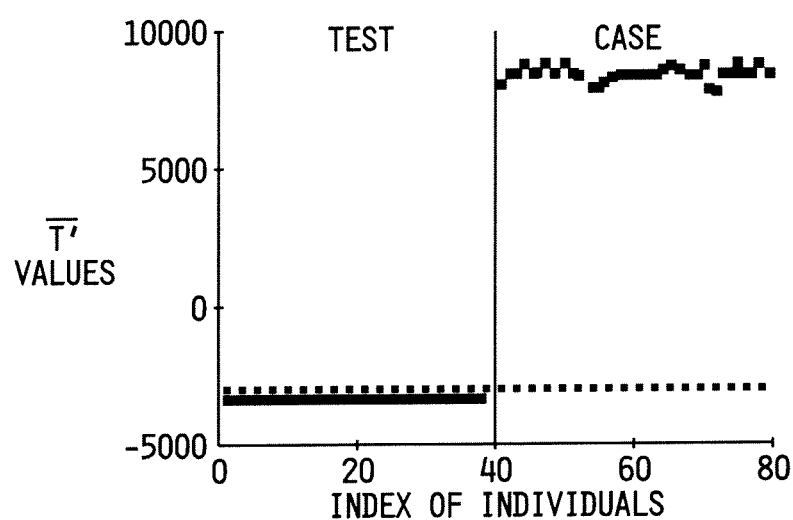
FIG. 4d is even yet another graph illustrating the power of the Homer-like statistic test and the likelihood ratio test in an experiment evaluating the re-identification powers of an adversary for distinguishing individuals from case and test groups.

This outcome was further compared with the identification powers the adversary may get in absence of the identification protections disclosed herein (i.e., when the DNA data of the case individuals was just aggregated according to the standard protection the NIH took before those two tests [Homer and likelihood ratio tests] were proposed for re-identification). Over the aggregated data, the adversary observes the allele frequencies of different SNPs, which is close to the situation when the 24-mers with different SNPs are all in different bins, and may therefore run both tests over these frequencies using the same background knowledge (the reference and the DNA sample from the testee). In the experiment disclosed herein, these tests were run on the SNPs of the same populations. The results, as presented in FIGS. 4c and 4d, show that both tests easily separated the case and test populations. In contrast, these tests were completely ineffective upon the keyed hashes the disclosed system exposes to the public cloud (FIGS. 4a and 4b). This strongly indicates that the presently disclosed system and method offers effective protection against the most powerful known re-identification attacks.

The above disclosure demonstrates that the 1-mer based near-optimal statistics have no power at all, indicating that the frequency analysis on the keyed-hash values of 1-mers does not offer sufficient information for a re-identification attack. As described herein, the Homer-like statistic cannot achieve a higher power on the combined seeds than on the continuous seeds. The similar analysis may be applied to the log likelihood ratio test. Consider a continuous seed (24 bps) consisting of two consecutive 12-mers, one of which contains a SNP site (denoted as $\alpha_1$). Because each 100-bp window in the human genome contains at most one SNP site, totally there are 100-12=88 combined seeds within the same 100-bp window that contain the SNP site. All of them include $\alpha_1$, thus may be denoted as $\alpha_1\|\alpha_i$ ($i=2,\ldots,89$), and one of them is the continuous seed (denoted as $\alpha_1\|\alpha_2$). Let $B_{k(i)}$ ($i=2,\ldots,89$) be the bins for combined seeds $\alpha_1\|\alpha_i$ when $\alpha_1$ carries a major allele, and $B_K^1{}_{(i)}$ be the bins for $\alpha_1\|\alpha_i$ when $\alpha_1$ has a minor allele. Because all these seeds involve the same SNP site on the 12-mer $\alpha_1$, all the related seeds from the testee's genome must all carry the same allele, major or minor. Then, the numbers of 1-mers in the bins $B_k(i)$ and $B_k^1(_i)$ are equally deviated from their expected counts ($F_k(_2)$ and $F_k(_i)$, respectively) as compared to the number of 1-mers in the bins of the continuous seeds (i.e., $B_{k(2)}$ and $B_{k'(2)}$) deviated from their expected counts. Hence:

$$\Sigma_i(|p_{k(i)}-\overline{F}_{k(i)}|+|p_{k'(i)}-\overline{F}_{k'(i)}|)\approx 88\times(|p_{k(2)}-\overline{F}_{k(2)}|+|p_{k'(2)}-\overline{F}_{k'(2)}|), \text{ and } \Sigma_i(|p_{k(i)}-\bar{f}_{k(i)}|+|p_{k'(i)}-\bar{f}_{k'(i)}|)\approx 88\times(|p_{k(2)}-\bar{f}_{k(2)}|+|p_{k'(2)}-\bar{f}_{k'(2)}|). \quad \text{(Equation 4)}.$$

Therefore, the Homer-like statistic on the bins of all combined seeds will become: $T_{com}\approx 88\times T$ where T is the Homer-like statistic on the bins of continuous 24-bp seeds (as defined in Equation 1). This implies that, no matter the testee is a case individual or not, the test statistic on all combined 12-bp seeds ($T_{com}$) is a constant (88) times larger than the test statistic on the continuous 24-bp seeds T. As a result, at the same confidence level, $T_{com}$ cannot achieve higher power than T. Since T has little re-identification power, $T_{com}$ should not either.

The above analysis is based upon the assumption that different bins are independent from each other. This is not entirely true, as some 24-mers in two bins may actually be correlated. However, establishing such a correlation between the hash values of two 1-mers is by no means easy, particularly when the adversary only observes the hash values of a relatively small set of samples from a donor. By far the largest dataset from an individual contains no more than 10 million reads (of 100 bps long each), only $\gamma=4/600=1/150$ of the 24-mers on human genome. For example, consider two completely correlated 24-mers. This may occur when they contain alleles of the same SNP. If both share the same allele, they are positively correlated; otherwise, if one 24-mer contains the major allele and the other contains the minor allele, they are negatively correlated. To detect such correlations, the adversary may conduct a co-occurrence statistic test over individual donors' read datasets. To defeat this attack, reads from 20 individuals (sampled from 40 DNA sequences) may be aggregated in one read mapping task (a sequencing project typically involves more participants). After the aggregation, in a single sample (an aggregated dataset), no SNP site likely contains only minor alleles. The probability for this to happen is $<2^{-10}\approx 10^{-12}$, considering the minor allele frequency is $<0.5$. As a result, an adversary cannot perform a co-occurrence test across multiple samples (aggregated datasets) on two 24-mers with the same alleles (positively correlated) or different alleles of the same SNP (negatively correlated), because the adversary will observe the 24-mers with major alleles in each sample.

Alternatively, the adversary may attempt to correlate two 24-mers (which may be only partially correlated) through their relative frequencies across multiple samples. Here a sample referred to herein includes one individual's read data that contains the target 24-mers, and the frequency of the 24-mer is calculated over multiple such samples. Remember that given a 24-mer, the probability a read dataset includes it is only $\gamma=1/150$. The adversary needs a set of 10 samples with the 24-mer to calculate its frequency at the precision of one decimal digit and multiple sets to correlate two 24-mers. Due to the presence of 2% sequencing errors, the best correlation coefficient the adversary may get between a pair of completely correlated 24-mers is within ±0.5 because 40% of 24-mers contain an error at 2% error rate per nucleotide, and therefore their hash values will not be observed in the datasets. As a result, the adversary has to carry out a correlation test on at least 15 sets (i.e. 150 samples) to obtain a confidence level (P-value) of 0.05 based on the table of critical values for Pearson's correlation coefficient. Note that the confidence level becomes even lower when these 24-mers are not completely correlated. Therefore, assume the adversary has collected M samples, the probability for a pair of completely correlated 24-mers to be both observed in at least 150 (out of M) samples may be estimated by a normal approximation of the binomial distribution with $\mu=\sigma^2=\gamma\times M$. When M=10,000 (that is, 10,000 datasets), the probability of getting these 150 samples (with the error-free target 24-mer) from these datasets is negligible ($\approx 10^{-28}$) even when it is considered that a total of $24\times 14\times 10^8=3.4\times 10^6$ 24-mers are subject to this correlation analysis (there are 14 million SNP sites in the human genome, each associated with 24 24-mers). For the 24-mers not completely correlated, for example, those containing different SNPs, the probability to get 150 samples in 10,000 datasets is even lower, because the chance to have both 24-mers in one dataset becomes $(0.6\gamma)^2$. Therefore, even when the 2-combinations of all $3.4 \times 10^8$ 24-mers are considered, the probability to correlate any two of them using 10,000 datasets is well below $10^{-12}$. This is the best chance that the adversary may correlate a single pair of 24-mers (which is not enough for an identification). If such a risk is acceptable to the data owner, what the owner may do is re-hash the reference genome every 10,000 datasets. The cost for the update is small: SHA-1 took about 4,700 minutes of CPU time to hash the whole genome on a 8-core desktop (2.93 GHz Intel Xeon) and produced about 5 TB data; the average overheads are merely 28 seconds CPU time and 503 MB data transfer for each of the 10,000 datasets.

The system and method disclosed herein is based upon the well-known seed-and-extend strategy, which first matches a seed, a segment of a read with one-(d+1)th of the read's length given an edit distance d, to the substrings on the reference genome, and then extends from these substrings to align the whole read. The idea is to split the mapping task along these two stages, delegating them to public and private clouds respectively: the public cloud searches for the exact matches between the keyed hash values of seeds and substrings (called l-mers for a substring of length l) on the reference genome to determine the possible positions of reads, while the private cloud extends from these positions to find the optimal alignments of these reads. While a single extension operation (involving calculation of an edit distance under a threshold) is known to be extremely efficient (in linear time), a read-mapping task is typically burdened by a huge number of extensions that need to be made. Therefore, it is conceivable that once the seeding process yields only a few or even unique positions for each read, the workload of the extension stage, which is undertaken by the private cloud, becomes much lower than that of the public cloud. This, unfortunately, is not guaranteed by the traditional "seed and extend" approach, particularly when the seed is too short due to a relatively large edit distance (e.g., 6 for 100-bp reads). To address this challenge, the system and method disclosed herein utilizes seed combinations to ensure a small number of extensions for each read, at a spatial overhead that may be easily afforded by today's clouds. A security analysis for the disclosed system was conducted over the reference genome and a performance analysis on a cloud platform using real human microbiome datasets. The disclosed system mapped 10 million reads to the largest human chromosome within half an hour and outsourced over 98% of the mapping computation to the low-cost public cloud.

Most proposed techniques for secure outsourcing of genomic computations focus on new cryptographic primitives. For example, a privacy-preserving protocol for computing edit distances shares a matrix for dynamic programming to multiple servers, which need to collaborate with each other through homomorphic encryptions and oblivious transfers to calculate each matrix element. Such approach was found to need 5 and one half minutes to compute an instance of the size (25, 25). Another prominent example is the work on optimized SMC for DNA sequence alignment, which is designed to leverage the special features of dynamic programming to improve the performance of SMC. This approach is efficient, taking about 4.38 seconds and 4.38 MB communication to complete the aforementioned task. Still, such overheads make it hard to scale up to the bar of comparing millions of reads with millions to billions of l-mers. Recent developments on this line of research include oblivious automata evaluation, which only needs 0(n) modular exponentiations to work on the sequences with n elements. This performance, however, still cannot sustain the scale of a read-mapping task. Another recent proposal attempts to "disguise" DNA sequences by scrambling some of its nucleotides to produce multiple versions of the sequence and let multiple servers compute on them. The outcomes of these computations are then analyzed by the client to restore the edit distance between the sequence and an l-mer on the genome. The problem with this approach is that the server needs to communicate with the client for every alignment attempt, which makes its scalability questionable. Further, those approaches fail to take advantage of the special features of human genomes, which are utilized in the system and method disclosed herein for building the simple and practical solution provided herein.

Secret-sharing based approaches may bring in new policy challenges: once the data has been shared to multiple parties, the NIH completely loses the control of it, since these parties may work together to restore the data; it is still unclear whether the NIH needs to sign an agreement with each of them, which these parties may want to avoid for liability concerns, and if so, what the agreement will look like. This concern is also applied to the approaches such as distributed Smith-Waterman algorithm that decomposes a computation problem into small sub-problems and allocates them to multiple problem solvers, under the assumption that these parties will not collude. Another related approach lets the provider of genomic data replace the SNP values of the data with symbols, which allows an untrusted party to perform a program specialization on this sanitized data. The approach assumes that the data provider knows the locations of SNPs in its data, whereas reads do not carry such information before they are mapped onto the reference genome. Also somewhat related to the system and method described herein is the study on the information leaks caused by aligning a query sequence to those in a genomic database. A similar problem may occur when the public cloud starts analyzing the frequencies of the hash values of l-mers. Such a threat, however, is considered very limited. Regardless, the secure mapping system and method proposed herein is the first one that works on a large amount of read data and also achieve a high privacy assurance.

Secure computation outsourcing has been studied for more than a decade. Early research mainly focused on delegating cryptographic operations (e.g., modular exponentiations) to a set of untrusted helpers. More recent studies, including the techniques referred to herein, focus on securing computing of edit distances. Efforts have also been made to securely outsource other types of computations, for example, linear algebra operations and machine learning tasks. For example, Peer-for-Privacy decomposes a category of data mining algorithms into vector addition steps and distributes them to multiple nodes on a cloud, which may be securely evaluated through a special secret sharing scheme. All these approaches, however, are not be suitable for computing edit distances and incur large amounts of communication during the computation.

The system and method of the present disclosure prevents an adversary from inferring the rare alleles from the data on the public cloud (i.e. the keyed-hash values of the l-mers, not their content). Without known rare allele frequencies in a reference population, the hash values of these l-mers are indistinguishable from those not belonging to human, such as those of microbes. Further, although the copy number variations may be inferred from the data on the public cloud through frequency analysis, they are at much lower density in comparison to SNPs, and often show a continuous distribution. As a result, it is commonly believed that their identification power is much lower, and the threat may be mitigated by simple approaches like data aggregation. For example, the aggregation of sequences from any 20 individuals may result in the average copy number measures that are shared by different populations. So far, there are no known identification techniques using the copy number variations.

Provided herein is a new system and method that achieves secure and scalable read mapping on hybrid clouds. The disclosed system leverages the special features of the read mapping task, which only cares about small edit distances, and of the Cloud, which is good at handling a large amount of simple computation. These features enables the disclosed system to split the mapping computation according to the well-known "seed-and-extend" strategy wherein the seeding stage performs simple computation (exact matching) on a large amount of ciphertext, which is undertaken by the public cloud, and the extend stage involves a very small amount of relatively complicated computation (edit-distance calculation) at the genomic locations identified by the matches, which is shouldered by the private cloud. The present system and method moves the workload from the private cloud to the public cloud, while maintaining privacy protection and performance. The present disclosure shows that the approach, though simple, offers a high privacy assurance and may easily handle the computation of a practical scale.

EXAMPLES

1. Example #1.1

Security Analysis of the Disclosed System and Method

A security analysis of the disclosed system and method over the reference genome, particularly on the threat of frequency analysis, as the seeding happens over keyed-hash values for achieving a high performance was conducted. This risk, however, was found to be minimum in a whole genome analysis, due to the special structure of the human genome: most of its l-mers become unique when l grows over 20. A performance evaluation on the cloud platform with real human microbiome datasets further justified the efficacy of the disclosed approach, which mapped 10 million reads to the largest human chromosome within half an hour and outsourced over 98% of the mapping computation to the low-cost public cloud.

This evaluation was performed over a microbial filtering task. The sequences extracted from human microbes include the DNA information of their hosts, which, if not taken out, will not only contaminate the outcome of a microbiome analysis but also disclose the identities of the donors the microbes come from. Therefore, one of the most important read-mapping tasks is to compare the reads from microbiome datasets to the reference genome, to identify and remove those belonging to humans. For the time being, this task is still undertaken by the NIH internal servers, but there are demands to move the computation to the low-cost public cloud if the privacy of the donors may be protected.

A real microbiome dataset collected from a fecal sample of a human individual was utilized in the envelope. The dataset contains 10 million reads, totaling 250 MB, a data scale typical in today's microbe projects. 500,000 human reads collected from the reference genome were added to the datasets based on the experiments reported herein and a typical level of human contamination (4%) in microbiome data, as the original dataset, was already sanitized and being removed of human sequences. These human reads were randomly sampled from Chromosome 1 (Chr1), the largest chromosome with 252.4 million bps, and Chromosome 22 (Chr22), the smallest one with 52.3 million bps. They were further randomly adjusted to simulate a 3% sequencing error rate, and then mixed with the microbiome dataset respectively to build two test datasets.

These datasets were mapped on an NSF-sponsored large-scale cloud test-bed. The evaluation used 1 master node and 20 slave nodes as the public cloud. Each of these nodes had 8-core 2.93 GHz Intel Xeon, 24 GB memory, 862 GB local disk and Linux 2.6.18. The private cloud used herein was a single 8-core machine with the same hardware and software settings.

In the experiments, a prototype was run to filter the reads on the hybrid cloud, using edit distances of 3 and 6. The overheads incurred during each step of the computation was measured and compared with those of CloudBurst, a popular mapping software designed for the cloud platform. The experiment results are presented in Table 1 and Table 2, set forth below.

TABLE 1

Performance of Preprocessing and Seeding

| Chromosome (number of errors) | Data Preprocessing (Private Cloud) | | | Sort Plaintext and hashed Reference l-mers (Public cloud) | | Seeding (Public Cloud) | |
|---|---|---|---|---|---|---|---|
| | Fingerprint and compress reference l-mers (min:sec) | Hash seeds (1 core, min:sec) | | Compress plaintext l-mers (h:min:sec) | Sort hashed l-mers (h:min:sec) | Sort seed hashes (min:sec) | Merge query seeds to reference l-mers (min:sec) |
| Chr1 (3 errors) | 5:23 (1 core) | 1:01 | | 0:2:06 | 0:3:47 | 1:52 | 2:30 |
| Chr22 (3 errors) | 0:52 (1 core) | 1:03 | | 0:1:51 | 0:3:38 | 2:16 | 2:18 |
| Chr1 (6 errors) | 67:16 (8 cores) | 7:12 | | 3:48:11 | 3:35:27 | 3:9 | 10:22 |
| Chr22 (6 errors) | 13:10 (8 cores) | 7:08 | | 0:15:3 | 0:16:51 | 3:3 | 3:13 |

TABLE 2

Outsourced Computation

| Chromosome (# of errors) | Our Private Cloud Workload (sec) | Full Workload by Cloud Burst (sec) | Outsource Ratio (%) |
|---|---|---|---|
| Chr1 (3 errors) | 125 | 7520 | 98.34 |
| Chr22 (3 errors) | 63 | 1856 | 96.61 |
| Chr1 (6 errors) | 619 | 28504 | 97.83 |
| Chr22 (6 errors) | 168 | 6472 | 97.40 |

2. Example #1.2

Data Preparation

When the distance was 3,450,561,196 and 69,789,044 24-mers were extracted from Chr1 and Chr22 respectively. Those 24-mers were first compressed to remove duplicated sequences. This operation was performed on the public cloud: using 20 nodes, the compression was done within 126 seconds for Chr1 and 111 seconds for Chr22. Then, these unique 24-mers were hashed on the private cloud with SHA-1 using a 32-byte secret key. It took 323 seconds to work on Chr1 and 52 seconds on Chr22 using a single core. After that, these hashed reference sequences were moved back to the public cloud, which sorted them to prepare for the mapping task. As illustrated in Table 1, sorting brought in an overhead similar to that of compression. Note that all these operations only need to be performed once before the reference has to be replaced.

To work on the distance of 6, combinations of 12-mers which came from both chromosomes (39,649,379,528 from Chr1 and 6,141,430,152 from Chr22) were used. These 12-mers were combined within 100-bp windows, as described in the discussion regarding use of multiple seeds, and shipped to the public cloud for compression. The cloud spent almost 3.6 hours on Chr1 and roughly 15 minutes on Chr22. This is in a stark contrast to the difference in the time for processing these two references when the distance was 3. This study shows that the problem comes from Hadoop: its MapReduce operations involve a non-negligible workload for assigning jobs to individual nodes, monitoring the progress of their computations and coordinating their activities; therefore, when the job given to each node is relatively small, as in the case of processing the short Chr22, the computational time may be dominated by such overheads. Also noted herein is that this performance is by no means the best the Cloud may do. A much better performance may be expected from better sorting algorithms, such as TeraSort. These two sets of reference 24-mers were fingerprinted roughly within one hour by 8 cores, and their keyed-hash values were sorted within roughly the same amount of time as that for compression.

3. Example #1.3

Performance on the Public and Private Clouds

The study shows that seeding on the public cloud was extremely fast. The Hadoop-based prototype took less than 15 minutes to match all the seeds across the largest human chromosome, even when the edit distance reached 6, making 12-mer combinations about 88 times the size of the chromosome. Considering the 160 cores used, the consumption of total CPU time in such a computation is about 36 hours, which only costs about $3.60 on Amazon EC2. More specifically, sorting all the seeds or combined seeds took 111 to 210 seconds. A significant portion of such computational overheads, again, appear to come from Hadoop's management operations: for example, the time for sorting the combined seeds on Chr1 when the distance is 6 is almost identical to the time for the seeds when the distance is 3, though the former outnumber the latter by 6 to 1. This also happened to the merging step: when the distance is 3, it does not make much difference in time when merging the encrypted seeds with Chr1 or Chr22.

On the private cloud, about 60 seconds and about 420 seconds was spent hashing seeds and combined seeds respectively. The extension tasks, based upon matched seeds or combinations, were so small that they were all accomplished by a single core within 11 minutes (no more than 32 extensions per read). To understand how much computation this approach indeed outsourced to the public cloud, CloudBurst was run, a state-of-the-art cloud mapping software, on the microbiome dataset, using all 8 cores of the private cloud. As seen from Table 2, CloudBurst needs 8-hour CPU time to map the reads on Chr1 when the distance is 6, while the system and method disclosed herein consumed only 619 seconds to finish all extensions. In other words, about 97.8% of the overall computation load was outsourced to the public cloud.

4. Example #1.4

Discussion

The overall computation time (the time spent on the public cloud and the private cloud combined) of the prototype is 36.3 CPU hours for the mapping task on Chr 1 with an edit distance of 6, which is about 4.5 times as much as that for performing the whole computation on the private cloud, as measured from CloudBurst. However, considering the exceedingly low costs for the computation resources on the public cloud (as low as $0.10 per CPU hour on EC2), this hybrid-cloud based computation strategy may be highly cost-effective.

5. Example #2.1

Real Anonymization and Re-Identification

Simple anonymization techniques like aggregation have long been used to protect the privacy of genomic data. As a prominent example, Genome-Wide Association Studies (GWAS) typically use DNA microarrays to profile a set of pre-determined SNPs from a group of patients (called case) to study the genetic traits of their common disease. The SNPs from different case individuals were often aggregated into a mixture, from which nothing but the counts (or equivalently, the frequencies) of different SNP values (alleles) may be observed and used for statistical analysis. Such aggregate data was initially deemed safe to release in public environments. However, recent studies show that the data is actually vulnerable to a type of re-identification attacks given the allele frequencies of a reference population, which may be acquired from public sources such as the International Hap-Map Project, and a DNA sample from an individual, the individual's presence in the case population may be determined from the aggregate data through a statistical test.

6. Example #2.2

Anonymizing Read Data

Different from the microarray data that targets a specific set of SNPs, sequencing reads are randomly drawn from a human genome, which consists of 6 billion nucleotides. In a dataset with 1 million sequences of 100-bp long, about 0.3 of these reads carry SNPs, typically, one on each of them. These SNPs, roughly 0.02 of the total 14 million SNPs, may be viewed as randomly picked out from the whole SNP set. This ratio may become even lower when it comes to other human-related sequence datasets: a prominent example is human microbiome sequencing data, which is extracted from human microbes but also has about 1-8% of the reads contaminated from the respective human host. For such data, read mapping serves as an important step to remove the human contamination. Given that each random sample (all SNPs on the reads from one individual) is small relative to the total number of SNPs, the overlapping between two different persons' sequence datasets, in terms of the SNPs they share, is often not significant. Therefore, the question becomes, after aggregating multiple people's read datasets, each carrying a different set of SNPs, whether the resulting mixture may still be used to re-identify these individuals. This identification attempt may be made even more difficult to succeed by randomly adding to the mixture noise reads, which are randomly sampled from the reference genome with its SNP sites randomly set to major/minor alleles according to the known allele frequencies in human population (e.g. taken from the HapMap project), and/or by partitioning an individual's dataset into multiple subsets to let the public cloud process them separately.

7. Example #2.3

The Re-Identification Threat

Anonymization techniques seem to reduce the privacy risk involved in outsourcing the mapping computation to the public cloud. The disclosure and research shown herein, shows that a re-identification attack may still succeed on the anonymized read data in the presence of a reference population and a DNA sample from the victim. Specifically, consider a dataset whose sequencing reads are sampled from a population (referred to as the case group). According to the examples herein presented the allele frequencies in the case group are first estimated by aligning these reads to the reference genome: if a SNP site k has been covered by m reads, and i of them have the major allele and the rest carry the minor allele, the major allele frequency is calculated as $f_k=i/m$. Note that this frequency often deviates from the SNP's real major-allele frequency in the population simply because not everyone's SNP k has been sampled. Actually, it might well be that many SNP sites are not covered by any read and therefore have frequencies of zero. The case group here describes a group of human subjects whose reads are aggregated into the sequence dataset, as well as a mixture of real and fake humans, when artificial reads are added to the dataset as noise. In either case, one objective is to determine whether or not an individual (the testee) is present in the case group from the allele frequencies observed. To this end, a reference group is also needed, for example, the HapMap population whose allele frequency for each SNP k, Fk, is public knowledge, and a sequence of allele pairs from the testee, one pair for each of the SNP site k whose major-allele frequency Yk may be 0 (two minor alleles), 0.5 (one major and one minor) or 1 (two major). Based upon such information (access to which is deemed to be feasible), anonymized read data was analyzed using a very simple statistic as follows:

$$D_k = |Y_k - F_k| - |Y_k - f_k|$$ (Equation 5).

Assuming that the distributions of SNPs' allele frequencies in the case and reference populations are identical, the sum of $D_k$ across all independent SNP k will have a normal distribution, whose mean becomes zero when the testee is not in the case/reference groups, and significantly larger than zero when the testee is a case. By testing this statistic on the null hypothesis: "the testee is not within the case group," assessment of the level of privacy protection that different anonymization techniques are able to offer was performed. Note that although this statistic is well-known to be effective on the aggregated microarray data, the vulnerability of the anonymized sequence data to such a re-identification attack has not been investigated before.

To evaluate the re-identification risk in outsourcing anonymized read data, a series of hypothesis tests on such data, using the aforementioned test statistic was performed. Four scenarios were considered: 1) aggregation only, 2) noise-adding only, 3) aggregation and then data partition and 4) noise-adding and then data partition. All the genomic sequences used in this study were randomly sampled from the reference genome. When a sampled read covered a SNP site, its allele was randomly picked according to the major allele frequency of the site in the YRI population, as provided by the HapMap project. In this way, the realistic sequencing reads from a large group of simulated people was acquired. This example utilized published 3,138,397 SNP sites of the YRI population in the HapMap dataset.

An anonymized dataset with 100-bp reads was considered to be not secure if a sequence donor for the dataset has a probability of at least 0.1 to be identified with a confidence level no less than 0.99 (i.e. a false positive rate no more than 0.01). This analysis aims at determining the necessary condition, e.g., the minimum number of the personal datasets (the dataset of an individual's reads) needed to be aggregated or the noise reads needed to be added, to protect the person from being re-identified through her N SNPs in the dataset.

8. Example #2.4

Findings

Figure 5A:
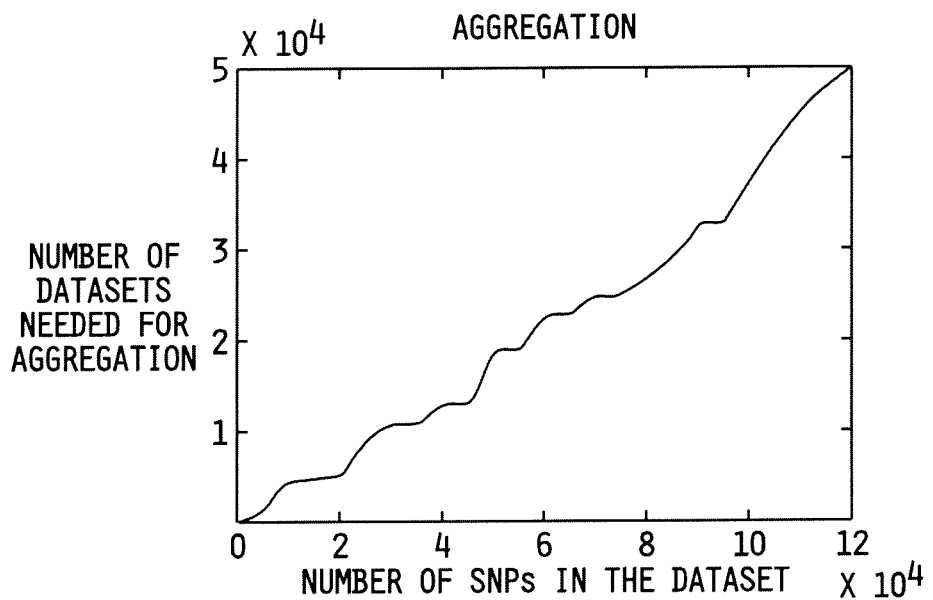
FIG. 5a is a graph showing the relationship between the number of personal datasets aggregated and the number of SNPs from each donor.

The outcomes of this evaluation study are presented graphically in FIGS. 5a-d. FIG. 5a shows the cost for the aggregation strategy. The simple test statistic in Equation 4 was found to be able to pose an alarming level of threat to the DNA donors, exactly as it does to the GWAS participants through their aggregated allele frequencies derived from microarray data. As illustrated in FIG. 5a, to cover the identity information disclosed by the N SNPs from each donor (x-axis), a large number of personal datasets (each with N SNPs) have to be aggregated (y-axis). As an example, consider a human microbiome sequencing dataset that contains 10 million reads with 3% of human contamination. These human reads cover about 100,000 SNPs, and therefore, according to FIG. 5a, need an aggregation of at least 38000 personal datasets of the same size to secure. This amount of data cannot be afforded by even the largest microbiome project, which sequenced fewer than 1000 individuals. Moreover, many microbiome sequencing datasets have a higher level of human contamination, not to mention human sequencing (e.g. genome-wide re-sequencing or exome sequencing) datasets with 70-80% human reads. The re-identification risk such data faces is certainly higher.

Figure 5B:
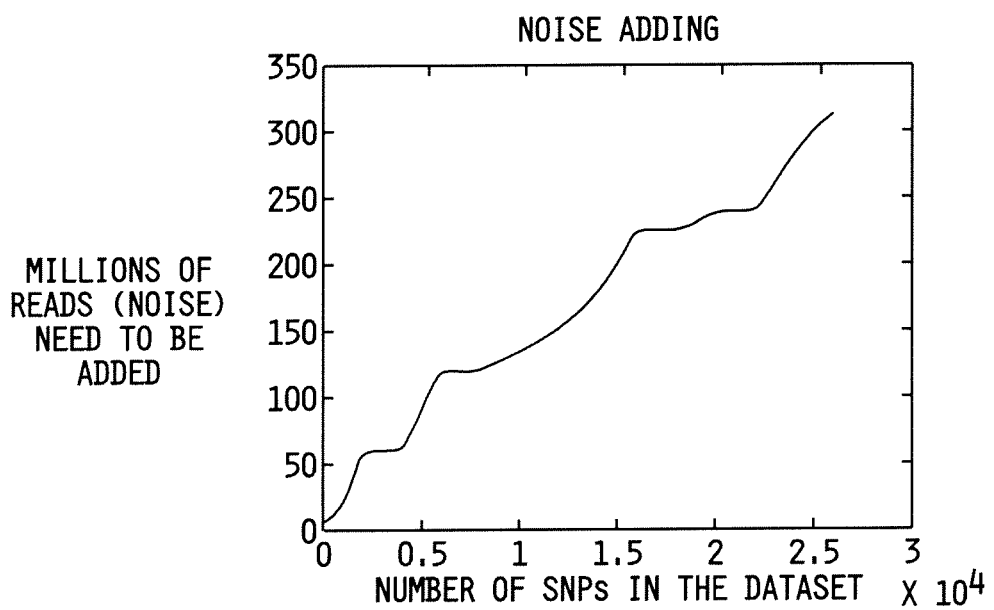
FIG. 5b is a graph showing the relationship between the number of noise reads per the number of SNPs from a donor securing the dataset.

Noise adding is another technique that may reduce the privacy risks in outsourcing read data. Noise reads covering major/minor alleles at randomly-chosen SNP sites were generated and the re-identification power that could be achieved over the personal dataset including these reads was evaluated. FIG. 5b shows the minimum number of noise reads (y-axis) that are required to secure the dataset with N SNPs from a donor (x-axis). This study shows that the number of the required noise reads grows linearly with regards to N. For example, at least 140 million noise reads need to be added in order to secure a human microbiome sequencing dataset with 10 million reads covering about 100,000 SNPs. Again, this estimation only describes the lower bound of the overhead for protecting the sequence data, as other read datasets often contain more human SNPs, particularly when most of their data comes from human (e.g. human re-sequencing data); in this case, the number of SNPs may increase by 20-30 times, which causes the amount of noise needed to suppress the identification power to rise significantly.

Figure 5C:
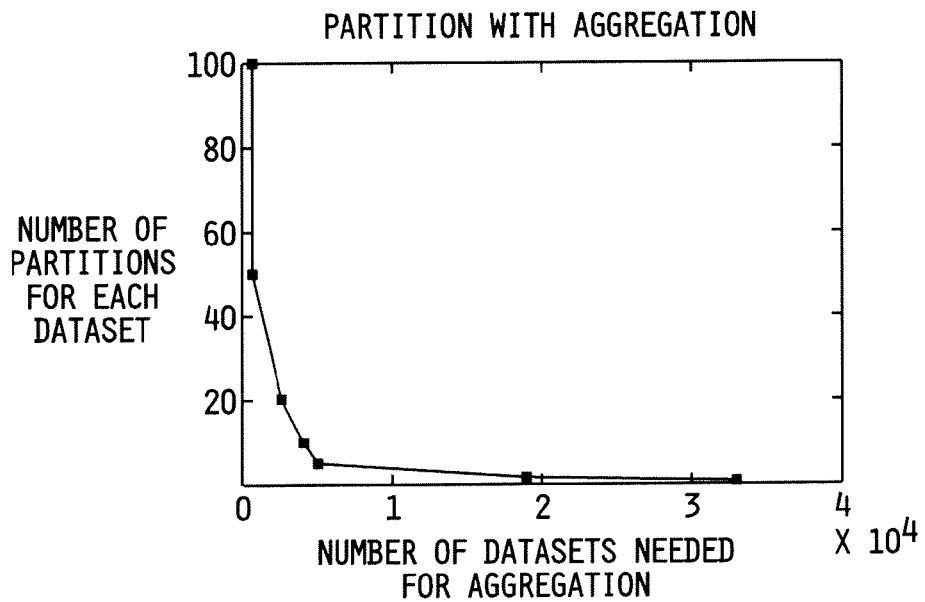
FIG. 5c is a graph showing the relationship between number of reads and the partitions of personal datasets.
Figure 5D:
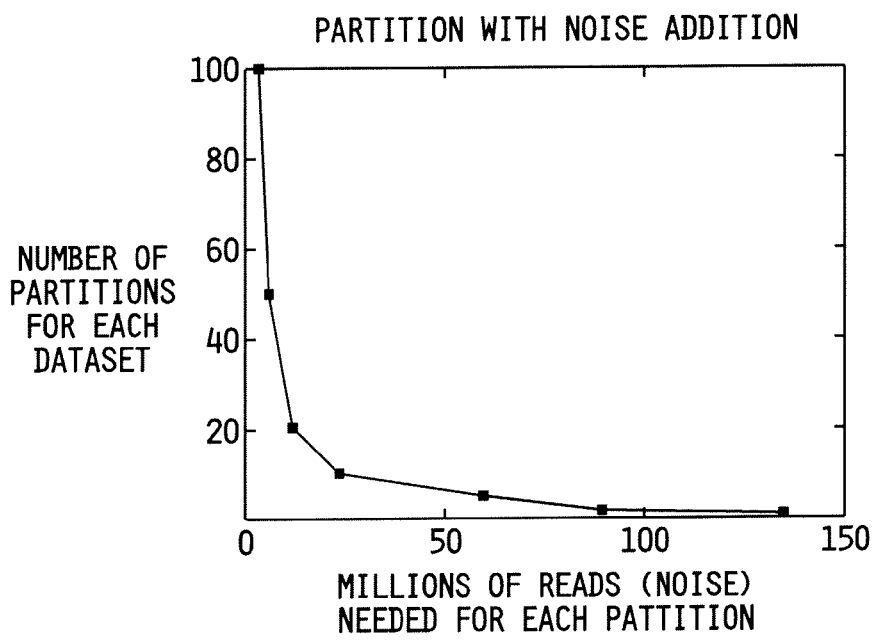
FIG. 5d is a graph showing the relationship between the number of partitions for each dataset and the number of reads per partition.

Additionally, the strategies that partition the datasets after they were anonymized through aggregation or noise adding were also studied herein. All these analyses were performed on the personal dataset that contained 10 million reads and covered about 100,000 human SNP sites, a large case in human microbiome sequencing. FIG. 5d shows the number of partitions needed (y-axis) to secure a dataset aggregated over different numbers of personal datasets (x-axis), and FIG. 5c demonstrates the number of required partitions (y-axis) vs. the number of noise reads being added (x-axis). As illustrated by FIGS. 5c and 5d, when it is possible to partition an aggregated dataset into 100 subsets for the public cloud to process independently, the dataset should be built from at least 500 personal datasets, or carry at least 100 million noise reads (1 million noise reads per subset) to stay safe, which are better than aggregation or noise adding alone, though the overheads are still significant (particularly when it comes to other read datasets including higher levels of SNPs). Moreover, data partition could bring in large communication overheads, because each subset needs to be transferred to the public cloud separately. It is also less clear how to prevent the public cloud from linking different subsets together (e.g. based on the customers who submit the jobs): when this happens, the cloud may simply aggregate these subsets to perform a re-identification attack.

What is claimed is:

1. One or more non-transitory, computer-readable media comprising a first plurality of instructions that, when executed by a first plurality of processors of a private computing network, causes the private computing network to:
   partition each of a plurality of DNA sequence reads into a plurality of (d+2) seeds, where d is an integer;
   encrypt each of the plurality of seeds;
   transmit encrypted data representing each of the plurality of seeds to a public computing network;
   receive from the public computing network data indicating one or more positions where a reference genome matches at least two seeds of the plurality of seeds, the at least two seeds corresponding to same DNA sequence read; and
   extend the at least two seeds at each of the one or more positions where the reference genome matches the at least two seeds to determine whether the DNA sequence read corresponding to the at least two seeds aligns with the reference genome at each matched position with an edit distance less than or equal to the integer d.

2. The one or more non-transitory, computer-readable media of claim 1, wherein the first plurality of instructions, when executed by the first plurality of processors, further causes the private computing network to:
   divide the reference genome into a plurality of substrings, each of the plurality of substrings and each of the plurality of seeds being of equal length;
   encrypt each unique substring of the plurality of substrings; and
   transmit encrypted data representing each of the unique substrings to the public computing network.

3. The one or more non-transitory, computer-readable media of claim 2, wherein the first plurality of instructions, when executed by the first plurality of processors, further causes the private computing network to:
   encrypt each of the plurality of seeds by applying a keyed encryption algorithm to each of the plurality of seeds; and
   encrypting each unique substring of the plurality of substrings by applying the keyed encryption algorithm to each unique substring.

4. The one or more non-transitory, computer-readable media of claim 2, further comprising a second plurality of instructions that, when executed by a second plurality of processors of the public computing network, causes the public computing network to:
   compare the data representing each of the plurality of seeds to the data representing each of the unique substrings; and
   transmit data indicating which of the plurality of encrypted seeds matches which of the encrypted substrings to the private computing network.

5. The one or more non-transitory, computer-readable media of claim 1, wherein the first plurality of instructions, when executed by the first plurality of processors, causes the private computing network to partition each of the plurality of DNA sequence reads into (d+2) seeds that are each between ten and twenty base pairs in length.

* * * * *